United States Patent [19]

Oh-ishi et al.

[11] Patent Number: 4,521,430
[45] Date of Patent: Jun. 4, 1985

[54] 1,5-BENZOTHIAZEPIN-4-ONE, THEIR PHARMACEUTICAL COMPOSITOINS, AND METHODS OF USE

[75] Inventors: Tokuro Oh-ishi, Tokyo; Mikio Takeda; Hiromichi Nakajima, both of Urawa; Taku Nagao, Tokyo, all of Japan

[73] Assignee: Tanabe Seiyaku Co., Ltd., Osaka, Japan

[21] Appl. No.: 614,743

[22] Filed: May 25, 1984

[30] Foreign Application Priority Data

Jun. 11, 1983 [GB] United Kingdom ............... 8316032

[51] Int. Cl.³ .................. A61K 31/555; C07D 281/02
[52] U.S. Cl. .............................. 514/211; 260/239.3 B; 514/929
[58] Field of Search ................. 260/239.3 B; 424/275

[56] References Cited

FOREIGN PATENT DOCUMENTS 0081234 6/1983 European Pat. Off. ..... 260/239.3 B
1805714 6/1969 Fed. Rep. of Germany ... 260/239.3 B Primary Examiner—Robert T. Bond Attorney, Agent, or Firm—Scully, Scott, Murphy & Presser

[57] ABSTRACT

A compound of the formula:

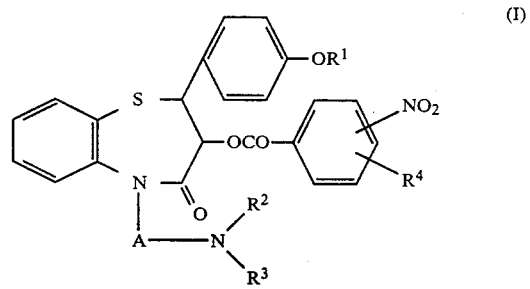

(I)

wherein $R^1$ and $R^2$ are each lower alkyl, $R^3$ is hydrogen, lower alkyl or hydroxy-lower alkyl, $R^4$ is hydrogen, halogen, lower alkyl, lower alkoxy, lower alkylthio or nitro, and A is lower alkylene, is disclosed. Said compound (I) and a pharmaceutically acceptable acid addition salt thereof are useful as cerebral or coronary vasodilators.

15 Claims, No Drawings

1,5-BENZOTHIAZEPIN-4-ONE, THEIR PHARMACEUTICAL COMPOSITOINS, AND METHODS OF USE

This invention relates to novel benzothiazepine derivatives and processes for preparing same. More particularly, it relates to a compound of the formula:

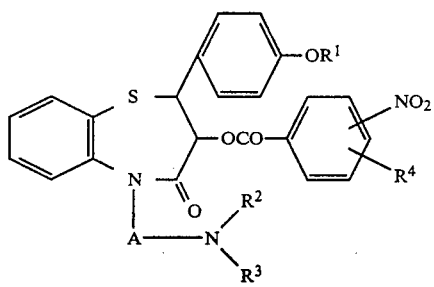
(I)

wherein $R^1$ and $R^2$ are each lower alkyl, $R^3$ is hydrogen, lower alkyl or hydroxy-lower alkyl, $R^4$ is hydrogen, halogen, lower alkyl, lower alkoxy, lower alkylthio or nitro, and A is lower alkylene, or a pharmaceutically acceptable acid addition salt thereof.

It is known that 2-(4-methoxyphenyl)-3-benzoyloxy-5-[2-(dimethylamino)ethyl]-2,3-dihydro-1,5-benzothiazepin-4(5H)-one and 2-(4-methoxyphenyl)-3-benzyloxy-5-[2-(dimethylamino)ethyl]-2,3-dihydro-1,5-benzothiazepin-4(5H)-one have a coronary vasodilating activity [Japanese Patent Publication (examined) Nos. 43784/1971 and 8544/1972)].

As a result of various investigations, we have now found that the compound (I) of the present invention shows a potent cerebral and/or coronary vasodilating activities without undesirable side effects such as inhibitory effect on atrioventricular conduction and heart rate-decreasing effect. For example, when the cerebral vasodilating activity is evaluated by examining vertebral artery blood flow in anesthetized dogs to which a test compound is intraarterially administered, said activity of (+)-cis-2-(4-methoxyphenyl)-3-(2-chloro-4-nitrobenzoyloxy)-5-[2-(dimethylamino)ethyl]-2,3-dihydro-1,5-benzothiazepin-4-(5H)-one fumarate is 4.5 times stronger than that of papaverine. On the other hand, the coronary vasodilating activity of (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate when examined by the Langendorff method using isolated hearts of guinea pigs is 10 times stronger than that of papaverine. Further, when administered intravenously to anesthetized guinea pigs, (+)-cis-2-(4-methoxyphenyl)-3-(2-chloro-4-nitrobenzoyloxy)-5-[2-(dimethylamino ethyl]-2,3-dihydro-1,5-benzothiazepin-4(5H)-one fumarate at a dose of 3 mg/kg did not induce disturbance of atrioventricular conduction.

We have also found that the compound (I) of the present invention shows a potent protective effect upon cerebral ischemia. For example, when the protective effect on cerebral ischemia was examined by occluding the common carotid and vertebral artery of rats to induce cerebral ischemia and then administering intraveneously a test compound to said rats (in this experiments, the cerebral blood flow was reestablished 10 minutes after the occlusion, and the administration of the test compound was begun 2 minutes before the reestablishment of the cerebral blood flow and continued at a rate of 0.1 mg/kg/minute), (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate showed about 50% recovery of electrocorticogram (ECoG) activity within one hour after the reestablishment.

The compound (I) is further characteristic in that said compound is low in toxicity. For example, the acute toxicity ($LD_{50}$) of (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate, when administered to mice orally, is more than 2 g/kg.

Representative examples of the compound of the present invention include those of the formula (I) in which $R^1$ is lower alkyl of one to 4 carbon atoms such as methyl, ethyl, propyl and butyl; $R^2$ is lower alkyl of one to 4 carbon atoms such as methyl, ethyl, propyl and butyl; $R^3$ is hydrogen, lower alkyl of one to 4 carbon atoms such as methyl, ethyl, propyl and butyl, or hydroxy-lower alkyl of one to 4 carbon atoms such as hydroxymethyl, 2-hydroxyethyl, 3-hydroxypropyl and 4-hydroxybutyl; $R^4$ is hydrogen, halogen such as chlorine, bromine and fluorine, lower alkyl of one to 4 carbon atoms such as methyl, ethyl, propyl and butyl, lower alkoxy of one to 4 carbon atoms such as methoxy, ethoxy, propoxy and butoxy, lower alkylthio of one to 4 carbon atoms such as methylthio, ethylthio, propylthio and butylthio, or nitro; and A is lower alkylene of one to 4 carbon atoms such as methylene, ethylene, trimethylene and tetramethylene. Among them, a preferred subgenus includes the compound of the formula (I) in which $R^1$ is methyl or ethyl, $R^2$ is methyl or ethyl, $R^3$ is hydrogen, methyl, ethyl, propyl or 2-hydroxyethyl, $R^4$ is hydrogen, chlorine, methyl, methoxy, methylthio or nitro, and A is ethylene or trimethylene. Another preferred subgenus is the compound of the formula (I) in which $R^1$ is methyl, ethyl, $R^2$ is methyl or ethyl, $R^3$ is hydrogen, methyl, ethyl, propyl or 2-hydroxyethyl, the group of the formula:

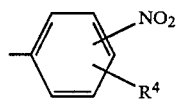

is 4-nitrophenyl, 3-nitrophenyl, 2-nitrophenyl, 2-chloro-4-nitrophenyl, 2-chloro-5-nitrophenyl, 4-chloro-2-nitrophenyl, 4-chloro-3-nitrophenyl, 5-chloro-2-nitrophenyl, 3-methyl-4-nitrophenyl, 3-methoxy-4-nitrophenyl, 2-methylthio-4-nitrophenyl, 2,4-dinitrophenyl or 3,4-dinitrophenyl, and A is ethylene or trimethylene. Other preferred subgenus is the compound of the formula (I) in which $R^1$ and $R^2$ are each methyl, $R^3$ is methyl or ethyl, the group of the formula:

is 4-nitrophenyl, 2-chloro-4-nitrophenyl, 4-chloro-2-nitrophenyl or 3-methyl-4-nitrophenyl, and A is ethylene. Further preferred subgenus is the compound of the formula (I) in which $R^1$, $R^2$ and $R^3$ are each methyl, the group of the formula:

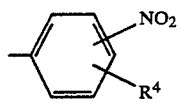

is 4-nitrophenyl, 2-chloro-4-nitrophenyl, 4-chloro-2-nitrophenyl or 3-methyl-4-nitrophenyl, and A is ethylene.

While the compound (I) of the present invention can exist in the form of two stereoisomers (i.e., cis and trans isomers) or four optical isomers (i.e., (+)-cis, (−)-cis, (+)-trans and (−)-trans isomers) due to the two asymmetric carbon atoms involved therein, all of four optical isomers or a mixture thereof are included within the scope of the invention. Among these isomers, however, cis isomer, especially (+)-cis isomer, of the compound (I) is preferred for medicinal use.

According to the present invention, the compound (I) can be prepared by condensing a compound of the formula:

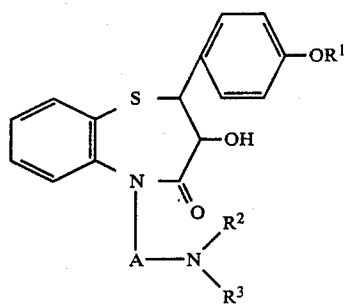

(II)

wherein $R^1$, $R^2$, $R^3$ and A are the same as defined above, or a salt thereof with a compound of the formula:

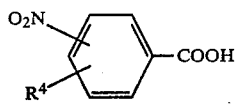

(III)

wherein $R^4$ is the same as defined above, or a reactive derivative thereof.

Alternatively, the compound (I) can be prepared by condensing a compound of the formula:

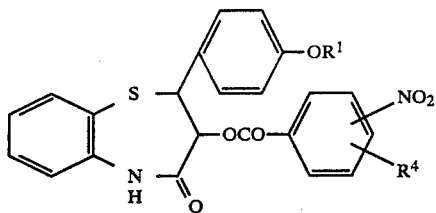

(IV)

wherein $R^1$ and $R^4$ are the same as defined above, or a salt thereof with a compound of the formula:

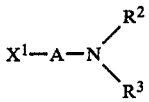

(V)

wherein $X^1$ is halogen, and $R^2$, $R^3$ and A are the same as defined above, or a salt thereof.

Further, the compound (I) in which $R^3$ is hydrogen can be prepared by condensing a compound of the formula:

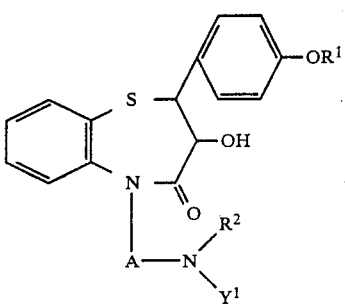

(VI)

wherein $R^1$, $R^2$ and A are the same as defined above and $Y^1$ is a protecting group, or a salt thereof with the compound (III) or a reactive derivative thereof to give a compound of the formula:

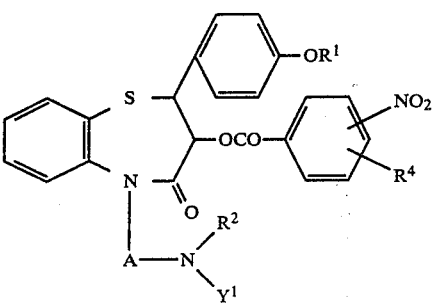

(VII)

wherein $R^1$, $R^2$, $R^4$, A and $Y^1$ are the same as defined above, and then removing the protecting group from the compound (VII) to give a compound of the formula:

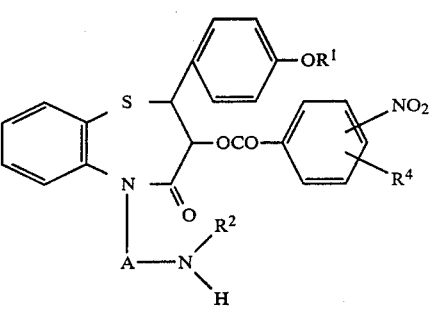

(I-a)

wherein $R^1$, $R^2$, $R^4$ and A are the same as defined above.

Additionally, the compound (I) in which $R^3$ is hydroxy-lower alkyl can be prepared by reacting the compound (I-a) or a salt thereof with a compound of the formula:

$$X^2\text{-B-}OY^2 \tag{VIII}$$

wherein $X^2$ is halogen, B is lower alkylene and $Y^2$ is hydrogen or a protecting group, to give a compound of the formula:

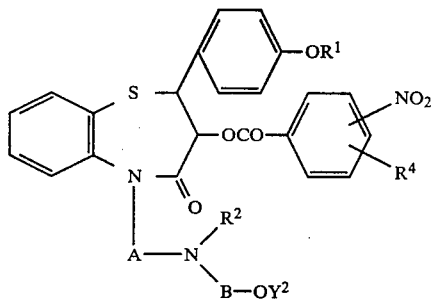
(IX)

wherein $R^1$, $R^2$, $R^4$, A, B and $Y^2$ are the same as defined above, and when $Y^2$ is the protecting group, further removing the protecting group from the compound (IX) to give a compound of the formula:

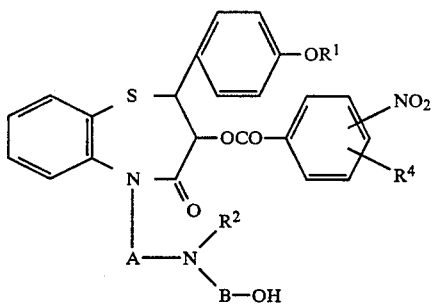
(I-b)

wherein $R^1$, $R^2$, $R^4$, A and B are the same as defined above.

The protecting group ($Y^1$) for amino group may be, for example, benzyloxycarbonyl, tert.-butoxycarbonyl, trityl, o-nitrophenylsulfenyl and the like. On the other hand, the protecting group ($Y^2$) for hydroxy group may be, for example, tetrahydropyran-2-yl, benzyloxycarbonyl, tert.-butoxycarbonyl, 2,2,2-trichloroethylcarbonyl, methoxymethyl, tert.-butyldimethyl-silyl and the like.

The starting compounds (II), (IV), (VI) and (I-a) may be in free form or in the form of a salt thereof. Examples of the salt of the compounds (II), (VI) and (I-a) include acid addition salts such as hydrochloride, hydrobromide and so forth. On the other hand, examples of the salt of the compound (IV) include alkali metal salts such as sodium salt or potassium salt. Further, the starting compound (V) may also be in free form or in the form of a salt thereof. Examples of the salt of the compound (V) include acid addition salts such as hydrochloride, hydrobromide and so forth.

The condensation reaction of the compound (II) or a salt thereof with the compound (III) may be conducted, for example, in the presence of a condensing agent in a solvent. The condensing agent may be, for example, dicyclohexylcarbodiimide, N,N'-diisopropylcarbodiimide and N,N'-di-p-tolylcarbodiimide. Methylene chloride, chloroform, ether, benzene, acetonitrile and dimethylformamide are examples of suitable solvents. It is preferred to carry out the reaction at a temperature of 0° to 30 °C.

Alternatively, the condensation reaction may be conducted, for example, by reacting the compound (II) or a salt thereof with a reactive derivative of the compound (III) in a solvent. The reactive derivative of the compound (III) may be, for example, the corresponding acid halides (e.g., chloride, bromide), acid anhydrides, mixed acid anhydrides (e.g., ethoxycarbonyl ester, isopropoxycarbonyl ester, isobutoxycarbonyl ester), active esters (e.g., p-nitrophenyl ester, 2,4,5-trichlorophenyl ester, 2,4,6-trichlorophenyl ester, N-hydroxysuccinimido ester, 1-benzotriazolyl ester). Methylene chloride, ether, acetone, dioxane, ethyl acetate, benzene, chloroform, acetonitrile and dimethylformamide are examples of suitable solvents. It is preferred to carry out the reaction at a temperature of 0° to 100° C., i.e., at a temperature of 0° to 30° C. if the compound (III) is used in the form of acid halide; at a temperature of 15° to 100° C. if the compound (III) is used in the form of acid anhydride; at a temperature of 0° to 30° C. if the compound (III) is used in the form of mixed acid anhydride; or at a temperature of 0° to 80° C. if the compound (III) is used in the form of active ester. When the compound (III) is used in the form of acid halide, it is also preferred to carry out the reaction in the presence of an acid acceptor. The acid acceptor may be, for example, pyridine, triethylamine, alkali metal carbonate (e.g., sodium carbonate, potassium carbonate), alkali metal bicarbonate (e.g., sodium bicarbonate, potassium bicarbonate) or alkali metal hydroxide (e.g., sodium hydroxide, potassium hydroxide).

The condensation reaction of the compound (IV) or a salt thereof with the compound (V) or a salt thereof may be carried out in a solvent. When the compound (IV) is used in free form, it is preferred to carry out the reaction in the presence of an alkali agent. The alkali agent may be, for example, alkali metal hydroxide (e.g., potassium hydroxide, sodium hydroxide), alkali metal carbonate (e.g., potassium carbonate, sodium carbonate) or alkali metal hydride (e.g., sodium hydride). Dimethylsulfoxide, dimethylformamide, 1,2-dimethoxyethane, dioxane, ethyl acetate and acetone are examples of suitable solvents. It is preferred to carry out the reaction at a temperature of 0° to 80° C.

The condensation reaction of the compound (VI) or a salt thereof with the compound (III) or a reactive derivative thereof may be carried out, for example, under the same conditions as employed in the condensation reaction of the compound (II) or a salt thereof with the compound (III) or a reactive derivative thereof.

Removal of the protecting group ($Y^1$) from the compound (VII) may be conducted, for example, by a conventional method. When the protecting group is benzyloxycarbonyl, tert.-butoxycarbonyl or trityl, for example, it is preferably removed by treating with an acid (e.g., hydrogen bromide-acetic acid, trifluoroacetic acid, trifluoromethanesulfonic acid). It is preferred to carry out the reaction at a temperature of −5° to 30° C. On the other hand, o-nitrophenylsulfenyl is preferably removed by treating with thiophenol, 2-mercaptopyridine or thioglycolic acid in the presence of an acid (e.g., acetic acid, hydrochloric acid) in a solvent (e.g., aqueous ethanol, ethanol, methylene chloride, ether) at a temperature of 0° to 40° C.

The reaction of the compound (I-a) or a salt thereof with the compound (VIII) may be conducted, for example, in the presence of an acid acceptor in a solvent. The acid acceptor may be, for example, alkali metal bicarbonate (e.g., sodium bicarbonate, potassium bicarbonate), alkali metal carbonate (e.g., sodium carbonate, potassium carbonate) or organic base (e.g., triethylamine, pyridine, diethylaniline). Acetone, acetonitrile, ethyl acetate, methanol, ethanol, methylene chloride, tetrahydrofuran, dioxane, dimethylformamide and dimethylsulfoxide are examples of suitable solvents. It is preferred to carry out the reaction at a temperature of 5° to 80° C.

Removal of the protecting group ($Y^2$) from the compound (IX) may be conducted, for example, by a conventional method. When the protecting group is tetrahydropyran-2-yl, benzyloxycarbonyl, tert.-butoxycarbonyl or methoxymethyl, for example, it is preferably removed by treating with an acid (e.g., hydrochloric acid, hydrogen bromide-acetic acid, p-toluenesulfonic acid, trifluoroacetic acid). It is preferred to carry out the reaction at a temperature of 5° to 50° C. in a solvent (e.g., ethanol, acetone, acetonitrile, dioxane). On the other hand, 2,2,2-trichloroethylcarbonyl is preferably removed by treating with zinc-ethanol at a temperature of 0° to 30° C. tert.-Butyldimethylsilyl may be removed by treating with tetrabutylammonium fluoride at a temperature of 0° to 30° C. in a solvent (e.g, acetonitrile, tetrahydrofuran, dioxane).

The starting compound (II), (IV), (VI) or (I-a) of the present invention involves four optical isomers (i.e., (+)-cis, (−)-cis, (+)-trans and (−)-trans isomers) due to the two asymmetric carbon atoms at the 2- and 3-positions of benzothiazepine skeleton. However, since all of the above-mentioned reactions of the invention can be carried out without racemization, the compound (I) of the present invention in an optically active form can be readily obtained by the use of an optically active isomer of the compound (II), (IV), (VI) or (I-a) as the starting material of the invention.

The compound (I) can be used for pharmaceutical use either as the free base or as an acid addition salt thereof. Pharmaceutically acceptable acid addition salts of the compound (I) are, for example, inorganic acid addition salts such as hydrochloride, hydrobromide, hydroiodide, perchlorate, sulfate or phosphate; and organic acid addition salts such as fumarate, maleate, oxalate, methanesulfonate, tartrate or succinate. These salts may be prepared, for example, by neutralizing the compound (I) with an acid. The compound (I) or a pharmaceutically acceptable acid addition salt thereof can be administered either orally or parenterally. Further, the compound (I) or its salt may be used in the form of a pharmaceutical preparation containing the same compound in conjunction or admixture with a pharmaceutical excipient suitable for oral or parenteral administration. Suitable excipients are, for example, starch, lactose, glucose, potassium phosphate, corn starch, arabic gum, stearic acid or other known medicinal excipient. The pharmaceutical preparation may be in solid form such as, for example, tablets, powder, capsules or granules; or in liquid form such as, for example, solutions or suspensions. Further, when administered parenterally the pharmaceutical preparation may be used in the form of injections.

As mentioned hereinbefore, the compound (I) of the present invention shows a potent cerebral or coronary vasodilating activity as well as a potent protective effect upon cerebral ischemia. In this connection, it is known that a calcium-antagonistic vasodilator such as 5-[(3,4-dimethoxyphenethyl)methylamino]-2-(3,4-dimethoxyphenyl)-2-isopropylvaleronitrile (the general name: verapamil) inhibits atrioventricular conduction to cause the prolongation of atrioventricular conduction time. Such conduction disturbance may sometimes induce arrhythmia. Unlike such known vasodilator, however, the compound (I) shows no substantial side effects (e.g., effect on atrioventricular conduction and heart rate) and at the same time is low in toxicity. Therefore, the compound (I) is characterized by its high therapeutic ratio of the cerebral or coronary vasodilating effect to the side effects (e.g., the inhibitory effect on atrioventricular conduction) and also by its great safety for use as a cerebral or coronary vasodilator. The compound (I) is useful for the treatment and/or prophylaxis of cerebral diseases such as cerebral vasospasm, cerebral ischemia or cerebral infarction; and heart diseases such as angina pectoris or myocardial infarction in a warm-blooded animal including human being.

Further, the compound (I) of the present invention has a potent platelets aggregation-inhibiting activity and a potent preventive effect upon lipid peroxide formation. In co-operation with the cerebral vasodilating activity, the platelets aggregation-inhibiting activity and preventive effect upon lipid peroxide formation may serve to treat cerebral diseases such as cerebral vasospasm, cerebral ischemia or cerebral infarction.

Moreover, the compound (I) of the present invention has a potent anti-calmodulin activity. Calmodulin inhibitors are reported to have vascular relaxing activity [cf. The Journal of Pharmacology and Experimental Therapeutics, 207, pp. 8–15(1978)] and blood platelets aggregation-inhibiting activity [cf. The Journal of Biological Chemistry, 256, pp. 12523–12528(1981); Nature, 287, pp. 863–865(1980)].

Therapeutic dose of the compound (I) or its salt depends on route of administration; the age, weight and condition of patients; and the particular disease to be treated. In general, however, it may be used at a dose of 0.05 to 10 mg/kg/day, especially at a dose of 0.5 to 10 mg/kg/day in the case of oral administration; or at a dose of 0.05 to 5 mg/kg/day in the case of parenteral administration (e.g., intravenous injection).

Among the starting compounds of the invention, the compounds (II) and (VI) may be obtained, for example, by condensing a compound of the formula:

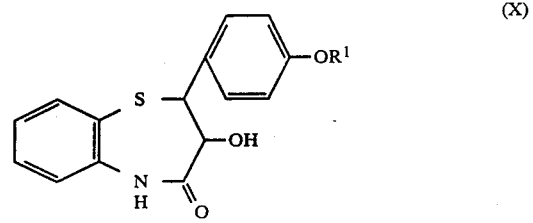

wherein $R^1$ is the same as defined above, with a compound of the formula:

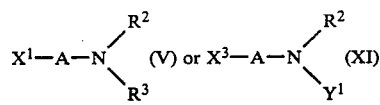

wherein $X^3$ is halogen, and $R^2$, $R^3$, A, $X^1$ and $Y^1$ are the same as defined above [Japanese Patent Publication (examined) Nos. 16749/1971 and 10544/1971; Chem. Pharm. Bull., 26, 2889 (1978)]. Alternatively, the compound (II) in which $R^3$ is lower alkyl may be obtained, for example, by removing the protecting group from the compound (VI) obtained above to give a compound of the formula:

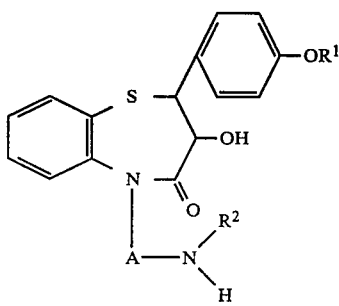

(XII)

wherein R¹, R² and A are the same as defined above [Chem. Pharm. Bull., 26, 2889 (1978)], and then reacting the compound with a compound of the formula:

$X^4$-$R^5$   (XIII)

wherein $X^4$ is halogen and $R^5$ is lower alkyl. Further, the compound (II) in which R¹ is lower alkyl other than methyl and R³ is lower alkyl may be obtained, for example, by treating a compound of the formula:

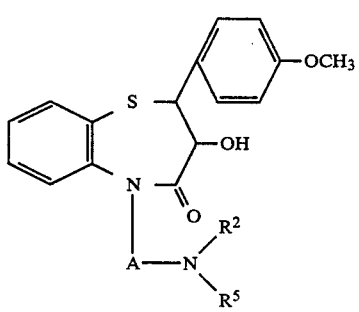

(XIV)

wherein R², R⁵ and A are the same as defined above, with boron tribromide to give a compound of the formula:

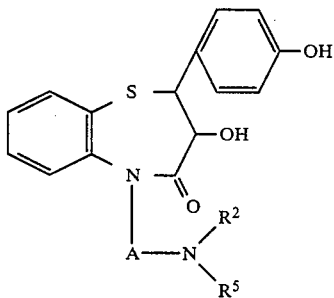

(XV)

wherein R², R⁵ and A are the same as defined above, and then reacting the compound (XV) with a compound of the formula:

$(R^6)_2SO_4$   (XVI)

wherein R⁶ is lower alkyl other than methyl.

On the other hand, the starting compound (IV) may be obtained, for example, by condensing the compound (X) with the compound (III) or a reactive derivative thereof in the same manner as employed in the condensation reaction of the compound (II) with the compound (III) or a reactive derivative thereof.

All of the aforementioned reactions can be carried out without racemization.

Practical and presently preferred embodiments of the present invention are illustrated in the following Experiments and Examples. Throughout the specification and claims, the terms "lower alkyl", "lower alkoxy", "hydroxy-lower alkyl", "lower alkylthio" and "lower alkylene" should be interpreted as referring to alkyl of one to 4 carbon atoms, alkoxy of one to 4 carbon atoms, hydroxyalkyl of one to 4 carbon atoms, alkylthio of one to 4 carbon atoms and alkylene of one to 4 carbon atoms, respectively.

Experiment 1

(Cerebral vasodilating activity)

Male dogs weighing 10 to 20 kg were anesthetized with sodium pentobarbital (30 mg/kg, intravenous injection). The blood flow in vertebral artery was measured continuously by means of an electromagnetic flowmeter under artificial respiration. A test compound dissolved in an aqueous 5% glucose solution was injected into vertebral artery. The cerebral vasodilating activity of the test compound was estimated in terms of "the potency ratio of said compound to papaverin" which was calculated from the dose-response curves thereof. Further, the cerebral vasodilating activity of the test compound was expressed as "—" if the potency ratio is less than 0.1; "±" if the potency ratio is not less than 0.1 but less than 1; "+" if the potency ratio is not less than 1 but less than 2; "++" if the potency ratio is not less than 2 but less than 3; and "+++" if the potency ratio is not less than 3.

The results are shown in the following Table 1.

TABLE 1

| Test compound | Cerebral vasodilating activity |
|---|---|
| (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate | +++ |
| (+)-cis-2-(4-methoxyphenyl)-3-(4-nitrobenzoyloxy)-5-[2-(dimethylamino)ethyl]-2,3-dihydro-1,5-benzothiazepin-4(5H)-one fumarate | +++ |
| (+)-cis-2-(4-methoxyphenyl)-3-(4-chloro-2-nitrobenzoyloxy)-5-[2-(dimethylamino)ethyl]-2,3-dihydro-1,5-benzothiazepin-4(5H)-one hydrochloride | +++ |
| (+)-cis-2-(4-methoxyphenyl)-3-(3-methyl-4-nitrobenzoyloxy)-5-[2-(dimethylamino)ethyl]-2,3-dihydro-1,5-benzothiazepin-4(5H)-one hydrochloride | +++ |
| (+)-cis-2-(4-methoxyphenyl)-3-(4-chloro-3-nitrobenzoyloxy)-5-[2-(dimethylamino)ethyl]-2,3-dihydro-1,5-benzothiazepin-4(5H)-one oxalate | +++ |
| (+)-cis-2-(4-methoxyphenyl)-3-(2-chloro-4-nitrobenzoyloxy)-5-[2-(diethylamino)ethyl]-2,3-dihydro-1,5-benzothiazepin-4(5H)-one hydrochloride | +++ |

Experiment 2

(Cerebral vasodilating activity)

Male dogs weighing 11 to 16 kg (one group: 3 dogs) were anesthetized with sodium pentobarbital (30 mg/kg, intravenous injection). The vertebral blood flow was measured by means of an electromagnetic flowmeter under artificial respiration. A test compound dissolved in an aqueous 5% glucose solution was injected intravenously at a dose of 0.2 mg/kg. The cerebral vasodilating activity of the test compound was estimated in terms of "total increase in vertebral blood flow" which was calculated by multiplying "increase ($\Delta$ml/minute) in blood flow at peak response" by "half duration time (T $\frac{1}{2}$:minute)".

Under this experiment, (+)-cis-(4-methoxyphenyl)-3-(2-chloro-4-nitrobenzolyloxy)-5-[2-(dimethylamino)ethyl]-2,3-dihydro-1,5-benzothiazepin-4(5H)-one fumarate showed the total increase of 91 ml in vertebral blood flow.

Experiment 3

(Coranary vasodilating activity)

Langendorff's method was used for testing the effect on the coronary blood flow of the isolated heart of guinea pig (about 280 g). The isolated heart was perfused with Locke-Ringer solution containing 2% of defibrinated rabbit blood, which had been saturated with a mixed gas of 95% $O_2$ and 5% $CO_2$ (30° C.). Perfusion pressure was kept at 40 cm $H_2O$. A solution of a test compound in an aqueous 5% glucose solution was injected into the perfusing solution at a volume of 0.1 ml per heart. The outflow of the perfusate was measured by means of a drop counter.

The coronary vasodilating activity of the test compound was expressed as "±" if the increase in coronary blood flow is less than 0.5 ml/minute at a dose of 100 μg/heart; "+" if the increase is not less than 0.5 ml/minute at a dose of 100 μg/heart; "++" if the increase is not less than 0.5 ml/minute at a dose of 30 μg/heart; and "+++" if the increase is not less than 0.5 ml/minute at a dose of not more than 10 μg/heart.

The results are shown in the following Table 2.

TABLE 2

| Test compound | Coronary vasodilating activity |
| --- | --- |
| (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate | +++ |
| (±)-cis-2-(4-methoxyphenyl)-3-(4-nitrobenzoyloxy)-5-[2-(dimethylamino)ethyl]-2,3-dihydro-1,5-benzothiazepin-4(5H)-one maleate | +++ |
| (+)-cis-2-(4-methoxyphenyl)-3-(4-nitrobenzoyloxy)-5-[2-(dimethylamino)ethyl]-2,3-dihydro-1,5-benzothiazepin-4(5H)-one fumarate | +++ |
| (+)-cis-2-(4-methoxyphenyl)-3-(4-chloro-2-nitrobenzoyloxy)-5-[2-(dimethylamino)ethyl]-2,3-dihydro-1,5-benzothiazepin-4(5H)-one hydrochloride | +++ |
| (+)-cis-2-(4-methoxyphenyl)-3-(3-methyl-4-nitrobenzoyloxy)-5-[2-(dimethylamino)ethyl]-2,3-dihydro-1,5-benzothiazepin-4(5H)-one hydrochloride | ... |

Experiment 4

(Platelet aggregation-inhibiting activity)

Blood was collected from the abdominal aorta of male Sprague-Dawley rats which were anesthetized with ether. Nine volumes of said blood were mixed with one volume of an aqueous 3.8% (w/v) trisodium citrate solution, and the mixture was centrifuged to give platelet-rich plasma ("PRP") as the supernatant solution. The bottom layer was further centrifuged to give platelet-poor plasma ("PPP") as the supernatant solution. Platelet counts were adjusted to $0.8-1 \times 10^6/mm^3$ for PRP by dilution with PPP. After a mixture of 200 μl of the diluted PRP and 25 μl of a test compound solution (final concentration: 100 μg/ml) was stirred for 2 minutes at 37° C., 25 μl of a collagen solution (Biochim. Biophys. Acta, 186, page 254(1969)) were added thereto. The degree of platelet aggregation was estimated by Born's method (Nature, 194, page 927(1962)) and percentage inhibition of platelet aggregation was calculated therefrom. The platelet aggregation-inhibiting activity of the test compound was expressed as (−) if the test compound showed less than 10% inhibition of platelet aggregation; (+) if the test compound showed not less than 10% inhibition of platelet aggregation but said percentage inhibition was lower than that of acetylsalicylic acid (100 μg/ml); or (++) if the test compound showed the platelet aggregation-inhibiting activity at least as strong as that of acetylsalicylic acid (100 μg/ml).

The results are shown in the following Table 3.

TABLE 3

| Test compound | Platelet aggregation-inhibiting activity |
| --- | --- |
| (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate | ++ |
| (+)-cis-2-(4-methoxyphenyl)-3-(4-nitrobenzoyloxy)-5-[2-(dimethylamino)ethyl]-2,3-dihydro-1,5-benzothiazepin-4(5H)-one fumarate | ++ |
| (±)-cis-2-(4-methoxyphenyl)-3-(2-nitrobenzoyloxy)-5-[2-(dimethylamino)ethyl]-2,3-dihydro-1,5-benzothiazepin-4(5H)-one hydrochloride | ++ |
| (+)-cis-2-(4-methoxyphenyl)-3-(3-methyl-4-nitrobenzoyloxy)-5-[2-(dimethylamino)ethyl]-2,3-dihydro-1,5-benzothiazepin-4(5H)-one hydrochloride | ++ |

Experiment 5

(Anti-calmodulin activity)

2 μg of calmodulin, 10 μg of phosphodiesterase, 0.1 mg of snake venom and a test compound were added to 0.8 ml of an aqueous solution (pH 7.5) containing 36 mM of tris-(hydroxymethyl)aminomethane, 36 mM of imidazole, 18 mM of magnesium chloride, 2 mM of ethylenediaminetetraacetic acid, 1.979 mM of calcium chloride and 50 mM of potassium chloride, and the mixture was shaken at 30° C. for 5 minutes. 0.2 ml of an aqueous cAMP (i.e., cyclic 3',5'-AMP) solution (final concentration of cAMP: 300 mM) was added to the mixture, and said mixture was shaken at 30° C. for 10 minutes. Then, 0.3 ml of an aqueous 30% trichloroacetic acid solution was added to the mixture to terminate the reaction. 0.2 ml of water was added to the mixture, and the test compound was extracted with one ml of chloroform. One ml of the aqueous layer was taken out, and 0.5 ml of an aqueous 4% molybdic acid solution and one ml of an aqueous 0.05% stannous chloride solution were added thereto. Optical density of the aqueous mixture was measured at 660 nm, and the phosphodiesterase activity (i.e., decomposition velocity of cAMP) was calculated therefrom. The anti-calmodulin activity of the test compound was estimated in-terms of "ID$_{50}$" (i.e., the concentration of the test compound which was necessary to induce 50% inhibition of the activation of phosphodiesterase activity by calmodulin).

The results are shown in the following Table 4.

TABLE 4

| Test compound | ID$_{50}$ ($\mu$M) |
| --- | --- |
| (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one fumarate | 2.5 |
| (+)-cis-2-(4-methoxyphenyl)-3-(4-nitrobenzoyloxy)-5-[2-(dimethylamino)ethyl]-2,3-dihydro-1,5-benzothiazepin-4(5H)-one fumarate | 4.5 |
| (+)-cis-2-(4-methoxyphenyl)-3-(3-methyl-4-nitrobenzoyloxy)-5-[2-(dimethylamino)ethyl]-2,3-dihydro-1,5-benzothiazepin-4(5H)-one hydrochloride | 2.5 |
| (+)-cis-2-(4-methoxyphenyl)-3-(3-methoxy-4-nitrobenzoyloxy)-5-[2-(dimethylamino)ethyl]-2,3-dihydro-1,5-benzothiazepin-4(5H)-one methanesulfonate | 2.7 |
| (+)-cis-2-(4-methoxyphenyl)-3-(4-chloro-3-nitrobenzoyloxy)-5-[2-(dimethylamino)ethyl]-2,3-dihydro-1,5-benzothiazepin-4(5H)-one oxalate | 1.4 |
| (+)-cis-2-(4-methoxyphenyl)-3-(2-chloro-4-nitrobenzoyloxy)-5-[2-(diethylamino)ethyl]-2,3-dihydro-1,5-benzothiazepin-4(5H)-one hydrochloride | 2.1 |
| (+)-cis-2-(4-methoxyphenyl)-3-(2-chloro-4-nitrobenzoyloxy)-5-[2-N—methyl-N—ethylamino)ethyl]-2,3-dihydro-1,5-benzothiazepin-4(5H)-one oxalate | 2.1 |

Example 1

3.72 g of (+)-cis-2-(4-methoxyphenyl)-3-hydroxy-5-[2-(dimethylamino)ethyl]-2,3-dihydro-1,5-benzothiazepin-4(5H)-one and 2.8 ml of triethylamine are dissolved in 30 ml of benzene, and 2.31 g of 2-chloro-4-nitrobenzoyl chloride are added thereto. The mixture is stirred at 25° C. for 30 minutes. After the reaction, the mixture is washed with water and an aqueous saturated sodium bicarbonate solution, successively. Then, the mixture is evaporated under reduced pressure to remove solvent. The residue is recrystallized from hot ethanol, whereby 5.13 g of (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one are obtained as pale yellow needles. Yield: 92%.

M.p. 156°–158° C.

$[\alpha]_D^{20}$ +75.20° (c=1.00, chloroform).

Fumarate:

colorless needles (recrystallized from acetone)

M.p. 152°–154.5° C.

$[\alpha]_D^{20}$ +38.80° (c=1.00, methanol).

Hydrochloride:

pale yellow powder (precipitated from a mixture of ether and isopropyl ether and isopropyl ether).

$[\alpha]_D^{20}$ +38.40° (c=1.0, methanol).

Analysis calculated for C$_{27}$H$_{26}$N$_3$O$_6$SCl.HCl.$\frac{1}{4}$H$_2$O C, 54.32; H, 4.64; N, 7.04, S, 5.37; Cl, 11.88. Found: C, 54.29; H, 4.85; N, 6.80; S, 5.25; Cl, 11.76.

Sulfamate: colorless needles (recrystallized from ethanol).

M.p. 153.5°–156.5° C.

$[\alpha]_D^{20}$ +34.20° (c=1.00, methanol).

Oxalate: Colorless needles (recrystallized from methanol).

M.p. 177°–179° C.

$[\alpha]_D^{20}$ +50.37° (c=1.06, dimethylformamide).

Example 2

0.04 g of 4-(dimethylamino)pyridine is added to a mixture of 1.2 g of (+)-cis-2-(4-methoxyphenyl)-3-hydroxy-5-[2-(dimethylamino)ethyl]-2,3-dihydro-1,5-benzothiazepin-4(5H)-one, 1.1 g of 2-chloro-4-nitrobenzoic acid, 0.76 g of dicyclohexylcarbodiimide and 20 ml of methylene chloride. The mixture is stirred for 4.5 hours under ice-cooling. After the reaction, the precipitates are removed by filtration. The filtrate is washed with an aqueous potassium carbonate solution and then with water, dried and then evaporated to remove solvent. The residue is crystallized with ethanol, whereby 1.68 g of (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one are obtained as pale yellow needles.

Yield: 94%

The physico-chemical properties of the product are identical with those of the product obtained in Example 1.

Example 3

1.2 g of (±)-cis-2-(4-methoxyphenyl)-3-hydroxy-5-[2-(dimethylamino)ethyl]-2,3-dihydro-1,5-benzothiazepin-4(5H)-one are dissolved in 15 ml of pyridine, and 0.66 g of 4-nitrobenzoyl chloride is added thereto under ice-cooling. The mixture is sirred at room temperature for 3 hours. After the reaction, the mixture is poured into ice-water, and then extracted with ethyl acetate. The extract is washed with water, dried and then evaporated to remove solvent. The residue is crystallized with a mixture of isopropyl ether and isopropanol, whereby 1.36 g of (±)-cis-2-(4-methoxyphenyl)-3-(4-nitrobenzoyloxy)-5-[2-(dimethylamino)ethy]-2,3-dihydro-1,5-benzothiazepin-4(5H)-one are obtained as yellow prisms.

Yield: 87%.

M.p. 122.5°–124° C.

Maleate: Colorless prisms (recrystallized from a mixture of methanol and ethanol).

M.p. 140°-142° C.
Analysis calculated for $C_{27}H_{27}N_3O_6S \cdot C_4H_4O_4 \cdot \frac{1}{2}H_2O$
C, 57.49; H, 5.14; N, 6.48; S, 4.95.
Found: C, 57.43; H, 5.04; N, 6.31; S, 5.00.

Example 4

1.2 g of (+)-cis-2-(4-methoxyphenyl)-3-hydroxy-5-[2-(dimethylamino)ethyl]-2,3-dihydro-1,5-benzothiazepin-4(5H)-one are dissolved in 20 ml of pyridine, and 0.66 g of 4-nitrobenzoyl chloride is added thereto under ice-cooling. The mixture is stirred at the same temperature for one hour. After the reaction, the mixture is poured into ice-water, and then extracted with ethyl acetate. The extract is washed with water, dried and then evaporated to remove solvent. The residue is crystallized with ethanol, whereby 990 mg of (+)-cis-2-(4-methoxyphenyl)-3-(4-nitrobenzoyloxy)-5-[-2-(dimethylamino)ethyl]-2,3-dihydro-1,5-benzothiazepin-4(5H)-one are obtained as pale yellow prisms. Yield: 59.3%.
M.p. 113°-114.5° C.
$[\alpha]_D^{20}$ +23.58° (c=1.09, chloroform).
Hydrochloride: pale yellow needles (recrystallized from ethanol).
M.p. 125.5°-127° C.
$[\alpha]_D^{20}$ +1.73° (c=1.04, methanol).
Analysis calculated for $C_{27}H_{27}N_3O_6S \cdot HCl \cdot C_2H_5OH \cdot \frac{1}{2}H_2O$ C, 56.81; H, 5.75; N, 6.85; S, 5.23.
Found: C, 56.50; H, 5.53; N, 6.23; S, 5.25.
Fumarate: colorless needles (recrystallized from ethanol).
M.p. 124.5°-127° C.
$[\alpha]_D^{20}$ +6.64° (c=0.994, methanol).
Analysis calculated for $C_{27}H_{27}N_3O_6S \cdot C_4H_4O \cdot H_2O$
C, 56.78; H, 5.07; N, 6.41; S, 4.89.
Found: C, 56.78; H, 4.94; N, 6.43; S, 4.92.

Example 5

3.73 g of (+)-cis-2-(4-methoxyphenyl)-3-hydroxy-5-[2-(dimethylamino)ethyl]-2,3-dihydro-1,5-benzothiazepin-4(5H)-one are dissolved in 20 ml of methylene chloride, and 1.01 g of sodium bicarbonate are added thereto. 1.95 g of 4-nitrobenzoyl chloride are gradually added at room temperature to the mixture under stirring, and said mixture is stirred at the same temperature for 4 hours. After the reaction, the mixture is washed with water, dried and then condensed. The residue is crystallized with ethanol, whereby 4.46 g of (+)-cis-2-(4-methoxyphenyl)-3-(4-nitrobenzoyloxy)-5-[2-(dimethylamino)ethyl]-2,3-dihydro-1,5-benzothiazepin-4(5H)-one are obtained as prisms. Yield: 73%.
M.p. 113°-114.5° C.

Example 6

11.2 g of (+)-cis-2-(4-methoxyphenyl)-3-hydroxy-5-[2-(dimethylamino)ethyl]-2,3-dihydro-1,5-benzothiazepin-4(5H)-one are dissolved in 100 ml of ethyl acetate, and 6.1 g of triethylamine are added thereto. 5.85 g of 4-nitrobenzoyl chloride are added to the mixture under ice-cooling and under stirring, and said mixture is stirred at room temperature overnight. After the reaction, the mixture is washed with water, dried and then evaporated to remove solvent. The residue is crystallized with ethanol, whereby 14.32 g of (+)-cis-2-(4-methoxyphenyl)-3-(4-nitrobenzoyloxy)-5-[2-(dimethylamino)ethyl]-2,3-dihydro-1,5-benzothiazepin-4(5H)-one are obtained. Yield: 91.5%.
M.p. 113°-114.5° C.

Example 7

11.2 g of (+)-cis-2-(4-methoxyphenyl)-3-hydroxy-5-[2-(dimethylamino)ethyl]-2,3-dihydro-1,5-benzothiazepin-4(5H)-one are dissolved in 120 ml of ethyl acetate, and 7.56 g of sodium bicarbonate are added thereto. 6.4 g of 4-nitrobenzoyl chloride are added to the mixture, and said mixture is stirred at room temperature overnight. After the reaction, the mixture is washed with water, dried and then evaporated to remove solvent. The residue is crystallized with ethanol, whereby 11.65 g of (+)-cis-2-(4-methoxyphenyl)-3-(4-nitrobenzoyloxy)-5-[2-(dimethylamino)ethyl]-2,3-dihydro-1,5-benzothiazepin-4(5H)-one are obtained. Yield: 74.4%.
M.p. 113°-114.5° C.

Example 8

11.2 g of (+)-cis-2-(4-methoxyphenyl)-3-hydroxy-5-[2-(dimethylamino)ethyl]-2,3-dihydro-1,5-benzothiazepin-4(5H)-one are dissolved in 120 ml of acetone, and 7.56 g of sodium bicarbonate are added thereto. 6.4 g of 4-nitrobenzoyl chloride are added to the mixture under ice-cooling and under stirring, and said mixture is stirred at room temperature for 2 hours. After the reaction, 10 ml of water are added to the mixture to dissolve inorganic materials, and said mixture is evaporated under reduced pressure to remove acetone. The oil thus obtained is extracted with ethyl acetate, and the extract is washed with water, dried and then eveporated to remove solvent. 9.3 g of (+)-cis-2-(4-methoxyphenyl)-3-(4-nitrobenzoyloxy)-5-[2-(dimethylamino)-ethyl]-2,3-dihydro-1,5-benzothiazepin-4(5H)-one are obtained.
Yield: 59.3%.
M.p. 113°-114.5° C.

Example 9

3.73 g of (+)-cis-2-(4-methoxyphenyl)-3-hydroxy-5-[2-(dimethylamino)ethyl]-2,3-dihydro-1,5-benzothiazepin-4(5H)-one are dissolved in 40 ml of acetone, and 2.07 g of potassium carbonate are added thereto. 2.04 g of 4-nitrobenzoyl chloride are added at room temperature to the mixture under stirring, and said mixture is stirred at the same temperature overnight. After the reaction, the mixture is treated in the same manner as described in Example 8. 3.8 g of (+)-cis-2-(4-methoxyphenyl)-3-(4-nitrobenzoyloxy)-5-[2-(dimethylamino)-ethyl]-2,3-dihydro-1,5-benzothiazepin-4(5H)-one are obtained.
Yield: 73%.
M.p. 113°-114.5° C.

Example 10

4.09 g of (+)-cis-2-(4-methoxyphenyl)-3-hydroxy-5-[2-(dimethylamino)ethyl]-2,3-dihydro-1,5-benzothiazepin-4(5H)-one hydrochloride are dissolved in 40 ml of water, and 80 ml of benzene are added thereto. Then, 0.86 g of sodium hydroxide is added to the mixture, and said mixture is stirred for 15 minutes. 2.05 g of 4-nitrobenzoyl chloride are added to the mixture under ice-cooling, and said mixture is stirred at the same temperature for 10 minutes and at room temperature for 1.5 hours. The benzene layer is collected, washed with water, dried and then evaporated to remove solvent. The residue is converted to its hydrochloride with hydrogen chloride-ethanol, whereby 2.12 g of (+)-cis-2-(4-methoxyphenyl)-3-(4-nitrobenzoyloxy)-5-[2-(dimethylamino)ethyl]-2,3-dihydro-1,5-benzothiazepin-4(5H)-one hydrochloride are obtained.

Yield: 38%.
M.p. 125.5°–127° C.

Example 11

1.24 g of (−)-cis-2-(4-methoxyphenyl)-3-hydroxy-5-[2-(dimethylamino)ethyl]-2,3-dihydro-1,5-benzothiazepin-4(5H)-one are dissolved in 15 ml of pyridine, and 0.62 g of 4-nitrobenzoyl chloride is added thereto under ice-cooling. The mixture is stirred at room temperature overnight. After the reaction, the mixture is poured into ice-water, and then extracted with benzene. The extract is washed with water, dried and then condensed under reduced pressure. The residue is purified by silica gel chromatography (solvent, chloroform: methanol=40:1), whereby 1.04 g of (−)-cis-2-(4-methoxyphenyl-3-(4-nitrobenzoyloxy)-5-[2-(dimethylamino)ethyl]-2,3-dihydro-1,5-benzothiazepin-4(5H)-one are obtained as pale yellow needles. Yield: 60%.

M.p. 108.5°–110.5° C.
$[\alpha]_D^{20} -23.8°$ (c=1.03, chloroform).

Fumarate: colorless prisms (recrystallized from ethanol).
M.p. 122°–125.5° C.
$[\alpha]_D^{20} -6.64°$ (c=1.0, methanol)
Analysis calculated for $C_{27}H_{27}N_3O_6S \cdot C_4H_4O_4 \cdot H_2O$
C, 56.78; H, 5.07; N, 6.41; S, 4.89. Found: C, 56.69; H, 4.91; N, 6.20; S, 4.73.

EXAMPLE 12

1.2 g of (±)-cis-2-(4-methoxyphenyl)-3-hydroxy-5-[2-(dimethylamino)ethyl]-2,3-dihydro-1,5-benzothiazepin-4(5H)-one are dissolved in 10 ml of pyridine, and 0.66 g of 3-nitrobenzoyl chloride is added thereto. The mixture is stirred at room temperature for one hour. After the reaction, the mixture is poured into ice-water. The crystalline precipitates are collected by filtration and then recrystallized from a mixture of ethyl acetate and n-hexane. 1.26 g of (±)-cis-2-(4-methoxyphenyl)-3-(3-nitrobenzoyloxy)-5-[2-(dimethylamino)-ethyl]-2,3-dihydro-1,5-benzothiazepin-4(5H)-one are obtained as colorless prisms. Yield: 75%.
M.p. 178.5°–179.5° C.

Fumarate: colorless needles (recrystallized from methanol)
M.p. 187°–189° C.

EXAMPLE 13

1.2 g of (±)-cis-2-(4-methoxyphenyl)-3-hydroxy-5-[2-(dimethylamino)ethyl]-2,3-dihydro-1,5-benzothiazepin-4(5H)-one are dissolved in 10 ml of pyridine, and 0.66 g of 2-nitrobenzoyl chloride is added thereto. The mixture is stirred at room temperature for 2 hours. After the reaction, the mixture is poured into ice-water. The crystalline precipitates are collected by filtration and then recrystallized from a mixture of ethyl acetate and n-hexane. 1.41 g of (±)-cis-2-(4-methoxyphenyl)-3-(2-nitrobenzoyloxy)-5-[2-(dimethylamino)ethyl]-2,3-dihydro-1,5-benzothiazepin-4(5H)-one are thereby obtained as colorless needles. Yield: 84%.
M.p. 161°–162.5° C.

Hydrochloride: colorless prisms (recrystallized from ethanol).
M.p. 237°–240° C. (decomp.)

EXAMPLE 14

0.04 g of 4-(dimethylamino)pyridine is added to a mixture of 1.2 g of (+)-cis-2-(4-methoxyphenyl)-3-hydroxy-5-[2-(dimethylamino)ethyl]-2,3-dihydro-1,5-benzothiazepin-4(5H)-one, 1.1 g of 4-chloro-2-nitrobenzoic acid, 0.76 g of dicyclohexylcarbodiimide and 20 ml of methylene chloride. The mixture is stirred for 3 hours under ice-cooling. After the reaction, the precipitates are removed by filtration. The filtrate is washed with an aqueous potassium carbonate solution and then with water, dried and then evaporated to remove solvent. The residue is crystallized with ethanol, whereby 1.36 g of (+)-cis-2-(4-methoxyphenyl)-3-(4-chloro-2-nitrobenzoyloxy)-5-[2-(dimethylamino)ethyl]-2,3-dihydro-1,5-benzothiazepin-4(5H)-one are obtained as pale yellow plates. Yield: 76%
M.p. 123.5°–125° C.
$[\alpha]_D^{20.5} +44.99°$ (c=1.10, chloroform).

Hydrochloride: crystalline powder (precipitated from isopropyl ether).
M.p. 125°–130° C. (decomp.)

EXAMPLE 15

0.04 g of 4-(dimethylamino)pyridine is added to a mixture of 1.2 g of (+)-cis-2-(4-methoxyphenyl)-3-hydroxy-5-[2-(dimethylamino)ethyl]-2,3-dihydro-1,5-benzothiazepin-4(5H)-one, 0.99 g of 3-methyl-4-nitrobenzoic acid, 0.76 g of dicyclohexylcarbodiimide and 30 ml of methylene chloride. The mixture is stirred at room temperature overnight. After the reaction, the precipitates are removed by filtration. The filtrate is washed with an aqueous potassium carbonate solution and then with water, dried and then evaporated to remove solvent. The residue is crystallized with isopropyl ether, whereby crystalline powder (M.p. 70°–73° C.) is obtained. The powder thus obtained is dissolved in a mixture of chloroform and methanol, and hydrogen chloride-ether is added to the solution. The precipitates are collected by filtration, whereby 1.45 g of (+)-cis-2-(4-methoxyphenyl)-3-(3-methyl-4-nitrobenzoyloxy)-5-[2-(dimethylamino)ethyl]-2,3-dihydro-1,5-benzothiazepin-4(5H)-one hydrochloride are obtained as white powder. Yield: 79%.
M.p. 139°–145° C. (decomp.).

Methanesulfonate: white powder (precipitated from isopropyl ether).
M.p. 110.5°–117° C. (decomp.).

Sulfamate: colorless needles (recrystallized from ethanol).
M.p. 112.5°–118° C.
$[\alpha]_D^{20} +12.73°$ (c=1.05, chloroform).

EXAMPLE 16

1.2 g of (+)-cis-2-(4-methoxyphenyl)-3-hydroxy-5-[2-(dimethylamino)ethyl]-2,3-dihydro-1,5-benzothiazepin-4(5H)-one, 1.08 g of 3-methoxy-4-nitrobenzoic acid and 0.96 g of dicyclohexylcarbodiimide are dissolved in a mixture of 30 ml of methylene chloride and 8 ml of dimethylformamide under ice-cooling. A catalytic amount of 4-(dimethylamino)pyridine is added to the solution, and said mixture is stirred at room temperature overnight. After the reaction, the precipitates are removed by filtration. The filtrate is washed with an aqueous potassium carbonate solution and then with water, dried and evaporated to remove solvent. The residue is purified by silica gel chromatography (solvent, chloroform:methanol=20:0.3). 1.2 g of (+)-cis-2-(4-methoxyphenyl)-3-(3-methoxy-4-nitrobenzoyloxy)-5-[2-(dimethylamino)ethyl]-2,3-dihydro-1,5-benzothiazepin-4(5H)-one are thereby obtained as an oil. Yield: 67.4%.

Methanesulfonate: white powder (precipitated from isopropyl ether).

M.p. 105°-112° C. (decomp.).

EXAMPLE 17

1.2 g of (+)-cis-2-(4-methoxyphenyl)-3-hydroxy-5-[2-(dimethylamino)ethyl]-2,3-dihydro-1,5-benzothiazepin-4(5H)-one, 1.16 g of 3,4-dinitrobenzoic acid and 0.76 g of dicyclohexylcarbodiimide are dissolved in 20 ml of methylene chloride, and the solution is stirred at room temperature overnight. After the reaction, the precipitates are collected by filtration. The filtrate is washed with water, dried and then evaporated to remove solvent. The residue is purified by silica gel chromatography (solvent, chloroform:methanol=100:3), whereby 0.8 g of (+)-cis-2-(4-methoxyphenyl)-3-(3,4-dinitrobenzoyloxy)-5-[2-(dimethylamino)ethyl]-2,3-dihydro-1,5-benzothiazepin-4(5H)-one is obtained as an oil.

Fumarate: yellow needles (recrystallized from ethanol).

M.p. 134°-136° C. (decomp.).

Analysis calculated for $C_{27}H_{26}N_4O_8S \cdot C_4H_4O_4 \cdot C_2H_5OH$ C, 54.39; H, 4.98; N, 7.69; S, 4.40. Found: C, 54.37; H, 4.98; N, 7.52; S, 4.45.

EXAMPLE 18

1.86 g of (+)-cis-2-(4-methoxyphenyl)-3-hydroxy-5-[2-(dimethylamino)ethyl]-2,3-dihydro-1,5-benzothiazepin-4(5H)-one are dissolved in 18 ml of pyridine, and 1.27 g of 4-chloro-3-nitrobenzoyl chloride are added thereto under ice-cooling. The mixture is stirred at room temperature for 2 hours. After the reaction, the mixture is poured into ice-water containing sodium bicarbonate and then extracted with ethyl acetate. The extract is washed with water, dried and evaporated to remove solvent. The residue is crystallized with a mixture of ethanol and isopropyl ether. The crude crystals (2.8 g) thus obtained are recrystallized from ethanol, whereby 2.7 g of (+)-cis-2-(4-methoxyphenyl)-3-(4-chloro-3-nitrobenzoyloxy)-5-[2-(dimethylamino)ethyl]-2,3-dihydro-1,5-benzothiazepin-4(5H)-one are obtained as yellow prisms.

M.p. 93°-96° C.

Oxalate: colorless prisms (recrystallized from ethanol).

M.p. 203°-205° (decomp.).

$[\alpha]_D^{20}+19.4°$ (c=1, methanol).

EXAMPLE 19

1.24 g of (+)-cis-2-(4-methoxyphenyl)-3-hydroxy-5-[2-(dimethylamino)ethyl]-2,3-dihydro-1,5-benzothiazepin-4(5H)-one are dissolved in 10 ml of methylene chloride, and 0.5 ml of triethylamine is added thereto. A solution of 0.88 g of 2-chloro-5-nitrobenzoyl chloride in 5 ml of methylene chloride is dropwise added to the mixture under ice-cooling, and said mixture is stirred at room temperature for one hour. After the reaction, the mixture is evaporated to remove solvent. The residue is extracted with ethyl acetate, and the extract is washed with water, dried and then evaporated to remove solvent. The crude product thus obtained is recrystallized from ethanol, whereby 1.71 g of (+)-cis-2-(4-methoxyphenyl)-3-(2-chloro-5-nitrobenzoyloxy)-5-[2-(dimethylamino)ethyl]-2,3-dihydro-1,5-benzothiazepin-4(5H)-one are obtained as yellow plates. Yield: 92%.

M.p. 169°-170° C.

$[\alpha]_D^{20}+98.4°$ (c=1, chloroform).

Oxalate: colorless prisms (recrystallized from methanol).

M.p. 223°-225° C. (decomp.).

$[\alpha]_D^{20}+101.8°$ (c=1, dimethylformamide).

EXAMPLE 20

1.86 g of (+)-cis-2-(4-methoxyphenyl)-3-hydroxy-5-[2-(dimethylamino)ethyl]-2,3-dihydro-1,5-benzothiazepin-4(5H)-one and 1 ml of triethylamine are dissolved in 15 ml of methylene chloride, and 1.27 g of 5-chloro-2-nitrobenzoyl chloride are added thereto. The mixture is stirred at room temperature for one hour. After the reaction, the mixture is poured into ice-water and then extracted with ethyl acetate. The extract is washed with an aqueous sodium bicarbonate solution, water and an aqueous sodium chloride solution, successively. Then, the extract is evaporated to remove solvent, and the residue is crystallized with ethanol. 2.45 g of (+)-cis-2-(4-methoxyphenyl)-3-(5-chloro-2-nitrobenzoyloxy)-5-[2-(dimethylamino)ethyl]-2,3-dihydro-1,5-benzothiazepin-4(5H)-one are thereby obtained as colorless prisms. Yield: 88.1%.

M.p. 159°-160° C.

$[\alpha]_D^{20}+46.0°$ (c=1.0, methanol).

Hydrochloride: colorless prisms (recrystallized from isopropanol).

M.p. 194°-196° C.

$[\alpha]_D^{20}+34.2°$ (c=1.0, methanol).

EXAMPLE 21

1.86 g of (+)-cis-2-(4-methoxyphenyl)-3-hydroxy-5-[2-(dimethylamino)ethyl]-2,3-dihydro-1,5-benzothiazepin-4(5H)-one are dissolved in 15 ml of methylene chloride, and 2 ml of triethylamine are added thereto. 1.39 g of 2-methylthio-4-nitrobenzoyl chloride are added to the mixture under stirring, and the mixture is stirred at room temperature for one hour. After the reaction, the mixture is washed with water, dried and then evaporated to remove solvent. The residue is purified by silica gel chromatography (solvent, chloroform:methanol=50:1), whereby 2.0 g of (+)-cis-2-(4-methoxyphenyl)-3-(2-methylthio-4-nitrobenzoyloxy)-5-[2-(dimethylamino)ethyl]-2,3-dihydro-1,5-benzothiazepin-4(5H)-one are obtained as an oil. Yield: 70%.

Fumarate: yellow crystalline powder (precipitated from a mixture of acetone, isopropanol and isopropyl ether).

M.p. 112°-116° C.

$[\alpha]_D^{20}+22.03°$ (c=1.06, methanol).

EXAMPLE 22

1.86 g of (+)-cis-2-(4-methoxyphenyl)-3-hydroxy-5-[2-(dimethylamino)ethyl]-2,3-dihydro-1,5-benzothiazepin-4(5H)-one are dissolved in 20 ml of dry benzene, and 3 ml of triethylamine are added thereto. A solution of 1.38 g of 2,4-dinitrobenzoyl chloride in 5 ml of dry benzene is added to the mixture under stirring, and said mixture is stirred at room temperature for 0.5 hour. After the reaction, the mixture is washed with water, dried and then evaporated to remove solvent. The residue is recrystallized from a mixture of methylene chloride and ethanol, whereby 2.45 g of (+)-cis-2-(4-methoxyphenyl)-3-(2,4-dinitrobenzoyloxy)-5-[2-(dimethylamino)ethyl]-2,3-dihydro-1,5-benzothiazepin-4(5H)-one are obtained as yellow needles. Yield: 87%.

M.p. 153.5°-156.5° C.

$[\alpha]_D^{20}+48.63°$ (c=1.0, chloroform).

Hydrochloride: pale yellow powder (precipitated from isopropyl ether).

M.p. 114.5°-124° C.

$[\alpha]_D^{20}+53.40°$ (c=1.0, dimethylformamide).

EXAMPLE 23

(1) 2.0 g of (±)-cis-2-(4-methoxyphenyl)-3-hydroxy-5-[2-(methylamino)ethyl]-2,3-dihydro-1,5-benzothiazepin-4(5H)-one and 0.96 g of ethyl iodide are dissolved in 20 ml of dimethylformamide, and 1.16 g of potassium carbonate are added thereto. The mixture is stirred at room temperature overnight. After the reaction, the mixture is poured into ice-water and then extracted with ethyl acetate. The extract is washed with water, dried and then condensed, whereby (±)-cis-2-(4-methoxyphenyl)-3-hydroxy-5-[2-(N-methyl-N-ethylamino)ethyl]-2,3-dihydro-1,5-benzothiazepin-4(5H)-one is obtained as a yellow oil.

(2) The product (yellow oil) obtained in paragraph (1) is dissolved in 20 ml of pyridine, and 0.9 g of 4-nitrobenzoyl chloride is added thereto. The mixture is stirred at room temperature overnight. After the reaction, the mixture is poured into ice-water and then extracted with ethyl acetate. The extract is washed with water, dried and then condensed. The residue is crystallized with isopropanol, whereby 1.3 g of (±)-cis-2-(4-methoxyphenyl)-3-(4-nitrobenzoyloxy)-5-[2-(N-methyl-N-ethylamino)ethyl]-2,3-dihydro-1,5-benzothiazepin-4(5H)-one are obtained as pale yellow needles. Yield: 50%.

M.p. 138°–139.5° C.

Fumarate: colorless needles (recrystallized from methanol).

M.p. 130°–134° C.

Analysis calculated for $C_{28}H_{29}N_3O_6S.\frac{1}{2}C_4H_4O_4.CH_3OH.\frac{1}{2}H_2O$ C, 58.66; H, 5.72; N, 6.62; S, 5.05. Found: C, 58.36; H, 5.62; N, 6.56; S, 4.83.

EXAMPLE 24

(1) 2.0 g of (±)-cis-2-(4-methoxyphenyl)-3-hydroxy-5-[2-(methylamino)ethyl]-2,3-dihydro-1,5-benzothiazepin-4(5H)-one and 1.0 g of n-propyl iodide are dissolved in 25 ml of dimethylformamide, and 1.16 g of potassium carbonate are added thereto. The mixture is stirred at room temperature for 4 hours. After the reaction, the mixture is poured into ice-water and then extracted with ethyl acetate. The extract is washed with water, dried and then condensed, whereby (±)-cis-2-(4-methoxyphenyl)-3-hydroxy-5-[2-(N-methyl-N-n-propylamino)ethyl]-2,3-dihydro-1,5-benzothiazepin-4(5H)-one is obtained as a colorless oil.

(2) The product (colorless oil) obtained in paragraph (1) is dissolved in 20 ml of pyridine, and 0.84 g of 4-nitrobenzoyl chloride are added thereto. The mixture is stirred at room temperature overnight. After the reaction, the mixture is poured into ice-water and then extracted with ethyl acetate. The extract is washed with water, dried and then condensed. The residue is crystallized with isopropanol, whereby 1.25 g of (±)-cis-2-(4-methoxyphenyl)-3-(4-nitrobenzoyloxy)-5-[2-(N-methyl-N-n-propylamino)ethyl]-2,3-dihydro-1,5-benzothiazepin-4(5H)-one are obtained as pale yellow needles. M.P. 116°–118° C.

Fumarate: colorless needles (recrystallized from methanol).

M.p. 168.5°–170° C.

Analysis calculated for $C_{29}H_{31}N_3O_6S.C_4H_4O_4.\frac{1}{3}H_2O$ C, 59.00; H, 5.35; N, 6.26; S, 4.77. Found: C, 59.18; H, 5.71; N, 6.35; S, 4.89.

EXAMPLE 25

1.0 g of (±)-cis-2-(4-methoxyphenyl)-3-hydroxy-5-[2-(diethylamino)ethyl]-2,3-dihydro-1,5-benzothiazepin-4(5H)-one is dissolved in 15 ml of pyridine, and 0.51 g of 4-nitrobenzoyl chloride is added thereto. The mixture is stirred at room temperature for 4 hours. After the reaction, the mixture is poured into ice-water and then extracted with ethyl acetate. The extract is washed with water, dried and then evaporated to remove solvent. The residue is crystallized with a mixture of isopropanol and methanol, whereby 1.1 g of (±)-cis-2-(4-methoxyphenyl)-3-(4-nitrobenzoyloxy)-5-[2-(diethylamino)ethyl]-2,3-dihydro-1,5-benzothiazepin-4(5H)-one are obtained as yellow needles. Yield: 80%.

M.p. 144.5°–146° C.

Fumarate: colorless needles (recrystallized from a mixture of methanol and isopropyl ether).

M.p. 110°–115.5° C.

Analysis calculated for $C_{29}H_{31}N_3O_6S.\frac{1}{2}C_4H_4O_4.\frac{1}{2}CH_3OH.H_2O$. C, 58.96; H, 5.81; N, 6.55; S, 5.00. Found: C, 58.76; H, 5.72; N, 6.53. S, 5.07.

EXAMPLE 26

1.53 g of (+)-cis-2-(4-methoxyphenyl)-3-hydroxy-5-[2-(diethylamino)ethyl]-2,3-dihydro-1,5-benzothiazepin-4(5H)-one are dissolved in 8 ml of pyridine, and 1.0 g of 2-chloro-4-nitrobenzoyl chloride is added thereto. The mixture is stirred at room temperature for 18 hours. After the reaction, the mixture is poured into ice-water. The aqueous mixture is alkalized with sodium bicarbonate and then extracted with ethyl acetate. The extract is washed with water, dried and evaporated to remove solvent. The residue is purified by silica gel chromatography (solvent, chloroform:methanol=40:1), whereby 1.80 g of (+)-cis-2-(4-methoxyphenyl)-3-(2-chloro-4-nitrobenzoyloxy)-5-[2-(diethylamino)ethyl]-2,3-dihydro-1,5-benzothiazepin-4(5H)-one are obtained as a yellow oil. Yield: 88%.

$[\alpha]_D^{20} +52.9°$ (c=0.98, methanol).

Hydrochloride: yellow powder (precipitated from isopropyl ether).

M.p. 115°–125° C.

$[\alpha]_D^{20} +42.4°$ (c=0.96, methanol).

EXAMPLE 27

1.53 g of (+)-cis-2-(4-methoxyphenyl)-3-hydroxy-5-[2-(diethylamino)ethyl]-2,3-dihydro-1,5-benzothiazepin-4(5H)-one are dissolved in 8 ml of pyridine. A solution of 1.50 g of 4-chloro-2-nitrobenzoyl chloride in 2 ml of chloroform is added to the solution, and the mixture is stirred at room temperature for 20 hours. After the reaction, the mixture is poured into ice-water. The aqueous mixture is alkalized with sodium bicarbonate and then extracted with ethyl acetate. The extract is washed with water, dried and evaporated to remove solvent. The residue is purified by silica gel chromatography (solvent, chloroform:methanol=30:1), whereby 1.90 g of (+)-cis-2-(4-methoxyphenyl)-3-(4-chloro-2-nitrobenzoyloxy)-5-[2-(diethylamino)ethyl]-2,3-dihydro-1,5-benzothiazepin-4(5H)-one are obtained as a yellow oil. Yield: 93%.

$[\alpha]_D^{20} +13.9°$ (c=0.53, methanol).

Hydrochloride: pale yellow powder (precipitated from a mixture of ethyl acetate and isopropyl ether).

M.p. 120°–125° C.

$[\alpha]_D^{20} +0.89°$ (c=1.06, methanol).

EXAMPLE 28

(1) 5.05 g of potassium carbonate are added to a mixture of 10.0 g of (+)-cis-2-(4-methoxyphenyl)-3-hydroxy-2,3-dihydro-1,5-benzothiazepin-4(5H)-one, 5.52 g of 2-(N-methyl-N-ethylamino)ethyl chloride hydrochloride and 100 ml of acetone. The mixture is refluxed under stirring overnight. After the reaction, the mixture is condensed under reduced pressure. The residue is dissolved in a mixture of ethyl acetate and water. The ethyl acetate layer is collected, dried and then evaporated to remove solvent. The residue is converted to its hydrochloride and then recrystallized from isopropanol. 12.28 g of (+)-cis-2-(4-methoxyphenyl)-3-hydroxy-5-[2-(N-methyl-N-ethylamino)ethyl]-2,3-dihydro-1,5-benzothiazepin-4(5H)-one hydrochloride are thereby obtained as colorless prisms. Yield: 87%.

$[\alpha]_D^{20} + 135.79°$ (c = 1.13, methanol).

(2) A solution of 0.88 g of 2-chloro-4-nitrobenzoyl chloride in 3 ml of methylene chloride is dropwise added at room temperature to a mixture of 1.41 g of (+)-cis-2-(4-methoxyphenyl)-3-hydroxy-5-[2-(N-methyl-N-ethylamino)ethyl]-2,3-dihydro-1,5-benzothiazepin-4(5H)-one hydrochloride, 15 ml of methylene chloride and 1 ml of triethylamine. The mixture is stirred for one hour. After the reaction, the mixture is evaporated to remove solvent. The residue is extracted with ethyl acetate, and the extract is washed with water, dried and then evaporated to remove solvent. The oil thus obtained is converted to its oxalate and then recrystallized from ethanol. 1.83 g of (+)-cis-2-(4-methoxyphenyl)-3-(2-chloro-4-nitrobenzoyloxy)-5-[2-(N-methyl-N-ethylamino)ethyl]-2,3-dihydro-1,5-benzothiazepin-4(5H)-one oxalate are thereby obtained as colorless needles. Yield: 83.5%.

M.p. 205°–206° C. (decomp.)

$[\alpha]_D^{20} + 53.2°$ (c = 1, dimethylformamide).

EXAMPLE 29

A solution of 0.88 g of 4-chloro-2-nitrobenzoyl chloride in 3 ml of methylene chloride is added to a mixture of 1.41 g of (+)-cis-2-(4-methoxyphenyl)-3-hydroxy-5-[2-(N-methyl-N-ethylamino)ethyl]-2,3-dihydro-1,5-benzothiazepin-4(5H)-one hydrochloride, 15 ml of methylene chloride and 1 ml of triethylamine. The mixture is treated in the same manner as described in Example 28-(2). The crude product is converted to its oxalate and then recrystallized from methanol. 1.9 g of (+)-cis-2-(4-methoxyphenyl)-3-(4-chloro-2-nitrobenzoyloxy)-5-[2-(N-methyl-N-ethylamino)ethyl]-2,3-dihydro-1,5-benzothiazepin-4(5H)-one oxalate are thereby obtained as colorless prisms. Yield: 86.4%.

M.p. 218°–220° C. (decomp.).

$[\alpha]_D^{20} + 48.0°$ (c = 1, dimethylformamide).

EXAMPLE 30

(1) 5.05 g of potassium carbonate are added to a mixture of 10.0 g of (+)-cis-2-(4-methoxyphenyl)-3-hydroxy-2,3-dihydro-1,5-benzothiazepin-4(5H)-one, 6.57 g of 2-(N-methyl-N-n-propylamino)ethyl chloride hydrochloride and 100 ml of acetone. The mixture is refluxed under stirring overnight. After the reaction, the mixture is treated in the same manner as described in Example 28-(1). 12.3 g of (+)-cis-2-(4-methoxyphenyl)-3-hydroxy-5-[2-(N-methyl-N-n-propylamino)ethyl]-2,3-dihydro-1,5-benzothiazepin-4(5H)-one are thereby obtained as an oil. Yield: 92%.

Hydrochloride: white powder (precipitated from isopropyl ether).

M.p. 93°–100.5° C.

$[\alpha]_D^{20} + 110.23°$ (c = 1.0, methanol).

(2) A solution of 0.88 g of 2-chloro-4-nitrobenzoyl chloride in 3 ml of methylene chloride is added to a mixture of 1.34 g of (+)-cis-2-(4-methoxyphenyl)-3-hydroxy-5-[2-(N-methyl-N-n-propylamino)ethyl]-2,3-dihydro-1,5-benzothiazepin-4(5H)-one, 15 ml of methylene chloride and 0.5 ml of triethylamine. The mixture is stirred at room temperature for one hour. After the reaction, the mixture is evaporated to remove solvent. The residue is extracted with ethyl acetate, and the extract is washed with water, dried and then evaporated to remove solvent. The brown oil (2 g) thus obtained is converted to its oxalate and then recrystallized from ethanol. 1.97 g of (+)-cis-2-(4-methoxyphenyl)-3-(2-chloro-4-nitrobenzoyloxy)-5-[2-(N-methyl-N-n-propylamino)ethyl]-2,3-dihydro-1,5-benzothiazepin-4(5H)-one oxalate are thereby obtained as colorless prisms. Yield: 87.5%.

M.p. 164°–165° C. (decomp.).

$[\alpha]_D^{20} + 53.0°$ (c = 1, dimethylformamide).

EXAMPLE 31

A solution of 0.88 g of 4-chloro-2-nitrobenzoyl chloride in 3 ml of methylene chloride is added to a mixture of 1.34 g of (+)-cis-2-(4-methoxyphenyl)-3-hydroxy-5-[2-(N-methyl-N-n-propylamino)ethyl]-2,3-dihydro-1,5-benzothiazepin-4(5H)-one, 15 ml of methylene chloride and 0.5 ml of triethylamine. The mixture is treated in the same manner as described in Example 30-(2). The crude product is converted to its oxalate and then recrystallized from ethanol. 1.78 g of (+)-cis-2-(4-methoxyphenyl)-3-(4-chloro-2-nitrobenzoyloxy)-5-[2-(N-methyl-N-n-propylamino)ethyl]-2,3-dihydro-1,5-benzothiazepin-4(5H)-one oxalate are thereby obtained as colorless plates. Yield: 79.5%.

M.p. 202°–204° C. (decomp.).

$[\alpha]_D^{20} + 49.6°$ (c = 1, dimethylformamide).

EXAMPLE 32

(1) 3.01 g of (+)-cis-2-(4-methoxyphenyl)-3-hydroxy-2,3-dihydro-1,5-benzothiazepin-4(5H)-one and 1.74 g of 3-(dimethylamino)propyl chloride hydrochloride are dissolved in 30 ml of acetone, and 3.04 g of potassium carbonate are added thereto. The mixture is refluxed overnight under stirring. After the reaction, the mixture is condensed under reduced pressure, and the residue is dissolved in ethyl acetate and water. The ethyl acetate layer is collected, dried and then evaporated to remove solvent. 3.3 g of (+)-cis-2-(4-methoxyphenyl)-3-hydroxy-5-[3-(dimethylamino)-propyl]-2,3-dihydro-1,5-benzothiazepin-4(5H)-one are thereby obtained as an oil.

(2) The oil (3.3 g) obtained in paragraph (1) is dissolved in 15 ml of pyridine, and 1.74 g of 4-nitrobenzoyl chloride are added thereto. The mixture is stirred at room temperature for 2 hours. After the reaction, the mixture is poured into ice-water. The precipitates are collected by filtration, whereby (+)-cis-2-(4-methoxyphenyl)-3-(4-nitrobenzoyloxy)-5-[3-(dimethylamino)-propyl]-2,3-dihydro-1,5-benzothiazepin-4(5H)-one is obtained as powder. The product (powder) thus obtained is purified by silica gel chromatography (solvent, chloroform:methanol=40:1) and then treated with a mixture of hydrogen chloride, ether and isopropyl ether. 4.28 g of (+)-cis-2-(4-methoxyphenyl)-3-(4- nitrobenzoyloxy)-5-[3-(dimethylamino)propyl]-2,3-dihydro-1,5-benzothiazepin-4(5H)-one hydrochloride are thereby obtained as yellow powder. Yield: 75%.

M.p. >60° C. (decomp.) (precipitated from isopropyl ether).

Mass (m/e): 536 (M+).

EXAMPLE 33

(1) 12.8 g of (+)-cis-2-(4-methoxyphenyl)-3-hydroxy-5-[2-(dimethylamino)ethyl]-2,3-dihydro-1,5-benzothiazepin-4(5H)-one are dissolved in 250 ml of dichloromethane. A solution of 42.6 g of boron tribromide in 250 ml of dichloromethane is dropwise added to the solution at −50° C. for 15 minutes. The mixture is stirred at room temperature for 2 hours. After the reaction, the mixture is alkalized by adding an aqueous saturated sodium bicarbonate solution at a temperature below 10° C. The organic layer is collected, washed with water, dried and then evaporated to remove solvent. The residue is recrystallized from ethanol, whereby 11.2 g of (+)-cis-2-(4-hydroxyphenyl)-3-hydroxy-5-[2-(dimethylamino)ethyl]-2,3-dihydro-1,5-benzothiazepin-4(5H)-one are obtained as colorless needles. Yield: 91.8%.

M.p. 120°–123° C.

$[\alpha]_D^{20}+164.2°$ (c=1.0, methanol).

Hydrochloride: Colorless needles (recrystallized from ethanol).

M.p. 196°–197° C. (decomp.).

$[\alpha]_D^{20}+143.4°$ (c=1.0, water).

(2) To a mixture of 10 g of (+)-cis-2-(4-hydroxyphenyl)-3-hydroxy-5-[2-(dimethylamino)ethyl]-2,3-dihydro-1,5-benzothiazepin-4(5H)-one, 1.34 g of 60% sodium hydride, 5.13 g of diethyl sulfate and 200 ml of anhydrous tetrahydrofuran are added 200 ml of dimethylformamide under stirring. The mixture is stirred at room temperature for 2 hours. After the reaction, the mixture is condensed under reduced pressure. The residue is dissolved in ethyl acetate, and the solution is washed with an aqueous potassium carbonate solution and water, successively. Then, the solution is dried and evaporated to remove solvent. The residue is purified by silica gel chromatography (solvent, chloroform:methanol=50:1), whereby 8.0 g of (+)-cis-2-(4-ethoxyphenyl)-3-hydroxy-5-[2-(dimethylamino)ethyl]-2,3-dihydro-1,5-benzothiazepin-4(5H)-one are obtained as an oil. Yield: 74%.

Hydrochloride: colorless needles (recrystallized from a mixture of acetone and methanol).

M.p. 195°–197.5° C.

$[\alpha]_D^{20}+109.44°$ (c=1.04, methanol).

Analysis calculated for $C_{21}H_{26}N_2O_3S\cdot HCl\cdot\frac{1}{2}CH_3COCH_3\cdot\frac{1}{2}H_2O$. C, 58.61; H, 6.78; N, 6.08; S, 6.95; Cl, 7.69. Found: C, 58.31; H, 6.53; N, 6.19; S, 7.24; Cl, 7.83.

(3) 960 mg of (+)-cis-2-(4-ethoxyphenyl)-3-hydroxy-5-[2-(dimethylamino)ethyl]-2,3-dihydro-1,5-benzothiazepin-4(5H)-one are dissolved in 20 ml of anhydrous benzene, and 1 ml of triethylamine is added thereto. 510 mg of 4-nitrobenzoyl chloride are gradually added to the mixture under stirring, and said mixture is stirred at room temperature for 0.5 hour. After the reaction, the mixture is washed with water, dried and then condensed to dryness. The residue is recrystallized from ethanol, whereby 1.04 g of (+)-cis-2-(4-ethoxyphenyl)-3-(4-nitrobenzoyloxy)-5-[2-(dimethylamino)ethyl]-2,3-dihydro-1,5-benzothiazepin-4(5H)-one are obtained as colorless needles. Yield: 78%.

M.p. 140.5°–142° C.

$[\alpha]_D^{20}+19.41°$ (c=1.03, chloroform).

Oxalate: colorless needles (recrystallized from ethanol).

M.p. 158°–160.5° C.

$[\alpha]_D^{20}+18.51°$ (c=1.08, dimethylformamide).

EXAMPLE 34

1.04 g of (+)-cis-2-(4-ethoxyphenyl)-3-hydroxy-5-[2-(dimethylamino)ethyl]-2,3-dihydro-1,5-benzothiazepin-4(5H)-one are dissolved in 20 ml of anhydrous benzene, and 1 ml of triethylamine is added thereto. A solution of 0.62 g of 2-chloro-4-nitrobenzoyl chloride in 2 ml of anhydrous benzene is added to the mixture under stirring, and said mixture is stirred at room temperature for 0.5 hour. After the reaction, the mixture is washed with water, dried and condensed to dryness. The residue is recrystallized from ethanol, whereby 0.94 g of (+)-cis-2-(4-ethoxyphenyl)-3-(2-chloro-4-nitrobenzoyloxy)-5-[2-(dimethylamino)ethyl]-2,3-dihydro-1,5-benzothiazepin-4(5H)-one is obtained as pale yellow needles. Yield: 61%.

M.p. 103°–105° C.

$[\alpha]_D^{20}+68.39°$ (c=1.05, chloroform).

Oxalate: colorless needles (recrystallized from ethanol).

M.p. 177°–179.5° C.

$[\alpha]_D^{20}+45.20°$ (c=1.0, dimethylformamide).

EXAMPLE 35

0.5 ml of triethylamine is added to a solution of 430 mg of (+)-cis-2-(4-methoxyphenyl)-3-hydroxy-5-[2-(N-methyl-N-ethylamino)ethyl]-2,3-dihydro-1,5-benzothiazepin-4(5H)-one hydrochloride in 10 ml of methylene chloride, and 270 mg of 4-chloro-3-nitrobenzoyl chloride are added thereto under ice-cooling and stirring. The mixture is stirred at room temperature overnight. The mixture is washed with water, dried and then condensed under reduced pressure to dryness. The residue is dissolved in acetone, and 90 mg of oxalic acid are added thereto. The mixture is allowed to stand. Crystalline precipitates are collected by filtration and dried. 410 mg of (+)-cis-2-(4-methoxyphenyl)-3-(4-chloro-3-nitrobenzoyloxy)-5-[2-(N-methyl-N-ethylamino)ethyl]-2,3-dihydro-1,5-benzothiazepin-4(5H)-one oxalate are obtained as colorless needles. Yield: 61%.

M.p. 160.5°–162° C.

$[\alpha]_D^{20}+20.40°$ (c=0.5, methanol).

EXAMPLE 36

(1) 3.01 g of (+)-cis-2-(4-methoxyphenyl)-3-hydroxy-2,3-dihydro-1,5-benzothiazepin-4(5H)-one are dissolved in 50 ml of pyridine, and 2.31 g of 2-chloro-4-nitrobenzoyl chloride are added thereto under ice-cooling and stirring. The mixture is stirred at room temperature overnight. The mixture is poured into ice-water and then extracted with ethyl acetate. The extract is washed with 10% hydrochloric acid and water, dried and then evaporated under reduced pressure to remove solvent. The residue is purified by silica gel chromatography (solvent, chloroform:methanol=100:1). 4.81 g of (−)-cis-2-(4-methoxyphenyl)-3-(2-chloro-4-nitrobenzoyloxy)-2,3-dihydro-1,5-benzothiazepin-4(5H)-one are obtained as a pale yellow powder. Yield: 99%.

$[\alpha]_D^{20}-11.14°$ (c=1.03, chloroform).

IR $\nu_{max}^{CHCl_3}$ (cm$^{-1}$): 3390, 1740, 1695, 1610

NMR (CDCl$_3$)δ: 3.79 (s, 3H), 5.29 (d, 1H, J=7.2 Hz), 5.57 (d, 1H, J=7.2 Hz), 6.76–8.22 (m, 11H), 8.72 (broad, 1H).

Mass (m/e): 486 (M+), 484 (M+), 283 (base peak).

(2) 970 mg of (−)-cis-2-(4-methoxyphenyl)-3-(2-chloro-4-nitrobenzoyloxy)-2,3-dihydro-1,5-benzothiazepin-4(5H)-one are dissolved in 15 ml of acetone, and 690 mg of potassium carbonate and 375 mg of 2-(dimethylamino)ethyl chloride hydrochloride are added thereto. The mixture is refluxed for 6 hours under stirring. After the reaction, the mixture is evaporated under reduced pressure to remove solvent. Ethyl acetate is added to the residue, and the mixture is washed with water. The ethyl acetate solution is dried and evaporated under reduced pressure to remove solvent. The residue is dissolved in ethanol under heating, and the mixture is allowed to stand. Crystalline precipitates are collected by filtration and dried, whereby 810 mg of (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one are obtained as pale yellow needles. Yield: 73%.

M.p. 153°–155.5° C.

$[\alpha]_D^{20} + 72.94°$ (c=1.02, chloroform).

Fumarate:

M.p. 150.0°–153° C.

$[\alpha]_D^{20} + 36.60°$ (c=1.0, methanol).

EXAMPLE 37

970 mg of (−)-cis-2-(4-methoxyphenyl)-3-(2-chloro-4-nitrobenzoyloxy)-2,3-dihydro-1,5-benzothiazepin-4(5H)-one are dissolved in 20 ml of acetone, and 690 mg of potassium carbonate and 410 mg of 2-(N-methyl-N-ethylamino)ethyl chloride hydrochloride are added thereto. The mixture is refluxed for 3 hour under stirring. After the reaction, the mixture is evaporated under reduced pressure to remove solvent. Ethyl acetate is added to the residue, and the mixture is washed with water. The ethyl acetate solution is dried and evaporated under reduced pressure to remove solvent. 180 mg of oxalic acid and 15 ml of ethanol are added to the residue, and the mixture is heated to make a clear solution. The clear solution is allowed to stand. Crystalline precipitates are collected by filtration and dried, whereby 1.20 g of (+)-cis-2-(4-methoxyphenyl)-3-(2-chloro-4-nitrobenzoyloxy)-5-[2-(N-methyl-N-ethylamino)ethyl]-2,3-dihydro-1,5-benzothiazepin-4(5H)-one oxalate are obtained as colorless needles. Yield: 91%.

M.p. 198°–200.5° C. (decomp.).

$[\alpha]_D^{20} + 53.00°$ (c=1.0, dimethylformamide).

EXAMPLE 38

(1) 3.01 g of (+)-cis-2-(4-methoxyphenyl)-3-hydroxy-2,3-dihydro-1,5-benzothiazepine-4(5H)-one are dissolved in 50 ml of pyridine, and 2.31 g of 4-chloro-3-nitrobenzoyl chloride are added thereto under ice-cooling and stirring. The mixture is stirred at room temperature overnight. The mixture is poured into ice-water, and the aqueous mixture is extracted with ethyl acetate. The extract is washed with 10% hydrochloric acid and water, dried and then evaporated under reduced pressure to remove solvent. The residue is purified by silica gel chromatography (chloroform:methanol=100:1), whereby 3.68 g of (−)-cis-2-(4-methoxyphenyl)-3-(4-chloro-3-nitrobenzoyloxy)-2,3-dihydro-1,5-benzothiazepin-4(5H)-one are obtained as a colorless powder. Yield: 75%.

$[\alpha]_D^{20} - 63.01°$ (c=0.97, chloroform).

IR$\nu_{max}^{CHCl_3}$ (cm$^{-1}$): 3390, 1735, 1695, 1605.

NMR (CDCl$_3$)δ: 3.82 (s, 3H), 5.28 (d, 1H, J=7 Hz), 5.54 (d, 1H, J=7 Hz), 6.80–8.04 (m, 11H), 8.58 (broad, 1H).

Mass (m/e): 486 (M+), 484 (M+), 283 (base peak).

(2) 970 mg of (−)-cis-2-(4-methoxyphenyl)-3-(4-chloro-3-nitrobenzoyloxy)-2,3-dihydro-1,5-benzothiazepin-4(5H)-one are dissolved in 15 ml of acetone, and 690 mg of potassium carbonate and 375 mg of 2-(dimethylamino)ethyl chloride hydrochloride are added thereto. The mixture is refluxed for 7 hours under stirring. After the reaction, the mixture is evaporated under reduced pressure to remove solvent. Ethyl acetate is added to the residue, and the mixture is washed with water. The ethyl acetate solution is dried and evaporated under reduced prssure to remove solvent. The residue is purified by silica gel chromatography (solvent, chloroform:methanol=100:3), whereby 900 mg of (+)-cis-2-(4-methoxyphenyl)-3-(4-chloro-3-nitrobenzoyloxy)-5-[2-(dimethylamino)ethyl]-2,3-dihydro-1,5-benzothiazepin-4(5H)-one are obtained as a yellow oil. Yield: 81%.

Oxalate: M.p. 202°–204° C. (decomp.).

$[\alpha]_D^{20} + 18.60°$ (c=1.0, methanol).

EXAMPLE 39

970 mg of (−)-cis-2-(4-methoxyphenyl)-3-(4-chloro-3-nitrobenzoyloxy)-2,3-dihydro-1,5-benzothiazepin-4(5H)-one are dissolved in 20 ml of acetone, and 690 mg of potassium carbonate and 410 mg of 2-(N-methyl-N-ethylamino)ethyl chloride hydrochloride are added thereto. The mixture is refluxed for 3 hours under stirring. After the reaction, the mixture is evaporated under reduced pressure to remove solvent. Ethyl acetate is added to the residue, and the mixture is washed with water. The ethyl acetate solution is dried and evaporated under reduced pressure to remove solvent. 180 mg of oxalic acid and 10 ml of acetone are added to the residue, and the mixture is heated to make a clear solution. The clear solution is allowed to stand. Crystalline precipitates are collected by filtration and dried, whereby 1.06 g of (+)-cis-2-(4-methoxyphenyl)-3-(4-chloro-3-nitrobenzoyloxy)-5-[2-(N-methyl-N-ethylamino)ethyl]-2,3-dihydro-1,5-benzothiazepin-4(5H)-one oxalate are obtained as colorless needles. Yield: 80%.

M.p. 171°–173° C.

$[\alpha]_D^{20} + 22.40°$ (c=1.0, methanol).

EXAMPLE 40

15 g of (+)-cis-2-(4-methoxyphenyl)-3-hydroxy-5-[2-(N-methyl-N-benzyloxycarbonylamino)ethyl]-2,3-dihydro-1,5-benzothiazepin-4(5H)-one are dissolved in 60 ml of pyridine, and 5.94 g of 4-nitrobenzoyl chloride are added thereto under ice-cooling. The mixture is stirred at room temperature overnight. After the reaction, the mixture is poured into ice-water and then extracted with ethyl acetate. The extract is washed with water, dried and then evaporated to remove solvent. The oil thus obtained is dissolved in 70 ml of acetic acid, and the solution is ice-cooled. 100 ml of 25% hydrogen bromide-acetic acid are added to the solution, and the mixture is stirred at room temperature for 45 minutes. Ether is added to the mixture, and the precipitates (yellow powder) are collected by filtration, washed with ether and then dried under reduced pressure. 13.3 g of (+)-cis-2-(4-methoxyphenyl)-3-(4-nitrobenzoyloxy)-5-[2-(methylamino)-ethyl]-2,3-dihydro-1,5-benzothiazepin-4(5H)-one hydrobromide are thereby obtained.

The product is purified by neutralizing it with an aqueous 5% potassium carbonate solution and then converting the free base into its fumarate.

Fumarate: colorless needles (recrystallized from methanol).

M.p. 164°–167° C. (decomp.).

$[\alpha]_D^{20}+2.0°$ (c=1.0, methanol-chloroform (1:1)).

Analysis calculated for $C_{26}H_{25}N_3O_6S \cdot C_4H_4O_4 \cdot \frac{1}{2}H_2O$. C, 56.95; H, 4.78; N, 6.64; S, 5.07. Found: C, 56.77; H, 4.61; N, 6.66; S, 4.99.

EXAMPLE 41

1.1 g of (+)-cis-2-(4-methoxyphenyl)-3-(4-nitrobenzoyloxy)-5-[2-(methylamino)ethyl]-2,3-dihydro-1,5-benzothiazepin-4(5H)-one and 1.2 g of ethylene bromohydrin are dissolved in 15 ml of dimethylformamide, and 0.9 g of sodium bicarbonate is added thereto. The mixture is stirred at 50° C. for 8 hours. After cooling, the mixture is poured into ice-water and then extracted with ethyl acetate. The extract is washed with water, dried and then condensed under reduced pressure. The residue is crystallized with isopropanol, whereby 1.2 g of (+)-cis-2-(4-methoxyphenyl)-3-(4-nitrobenzoyloxy)-5-[2-(N-methyl-N-(2-hydroxyethyl)amino)-ethyl]-2,3-dihydro-1,5-benzothiazepin-4(5H)-one are obtained as pale yellow needles. Yield: theoretical.

M.p. 133°–136° C.

$[\alpha]_D^{20}+28.0°$ (c=1.0, chloroform).

EXAMPLE 42

5.88 g of (+)-cis-2-(4-methoxyphenyl)-3-(4-nitrobenzoyloxy)-5-[2-(methylamino)ethyl]-2,3-dihydro-1,5-benzothiazepin-4(5H)-one and 5.44 g of 2-(2-bromoethoxy)tetrahydropyrane are dissolved in 50 ml of dimethylformamide, and 3.86 g of sodium bicarbonate are added thereto. The mixture is stirred at 50° C. overnight. After cooling, the mixture is poured into ice-water and then extracted with benzene. The extract is washed with water, dried and then condensed under reduced pressure. The residue (i.e., (+)-cis-2-(4-methoxyphenyl)-3-(4-nitrobenzoyloxy)- 5-{2-[N-methyl-N-(2-(tetrahydropyran)-2-yl-oxy)ethyl)amino]ethyl}-2,3-dihydro-1,5-benzothiazepin-4(5H)-one) is dissolved in 100 ml of ethanol, and 53 ml of 1.5% hydrochloric acid are added thereto. The mixture is stirred at room temperature for 5 hours. After the reaction, the mixture is neutralized with an aqueous sodium bicarbonate solution and then extracted with ethyl acetate. The extract is treated in the same manner as described in Example 41, whereby 2.96 g of (+)-cis-2-(4-methoxyphenyl)-3-(4-nitrobenzoyloxy)-5-[2-(N-methyl-N-(2-hydroxyethyl)amino)ethyl]-2,3-dihydro-1,5-benzothiazepin-4(5H)-one are obtained. Yield: 79%.

M.p. 133°–136° C.

What we claim is:

1. A compound of the formula:

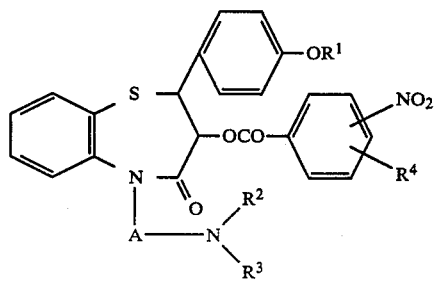

wherein $R^1$ and $R^2$ are each lower alkyl, $R^3$ is hydrogen, lower alkyl or hydroxy-lower alkyl, $R^4$ is hydrogen, halogen, lower alkyl, lower alkoxy, lower alkylthio or nitro, and A is lower alkylene, or a pharmaceutically acceptable acid addition salt thereof.

2. The compound claimed in claim 1, in which $R^1$ is methyl or ethyl.

3. The compound claimed in claim 2, in which $R^2$ is methyl or ethyl, $R^3$ is hydrogen, methyl, ethyl, propyl or 2-hydroxyethyl, $R^4$ is hydrogen, chlorine, methyl, methoxy, methylthio or nitro, and A is ethylene or trimethylene.

4. The compound claimed in claim 2, in which $R^2$ is methyl or ethyl, $R^3$ is hydrogen, methyl, ethyl, propyl or 2-hydroxyethyl, the group of the formula:

is 4-nitrophenyl, 3-nitrophenyl, 2-nitrophenyl, 2-chloro-4-nitrophenyl, 2-chloro-5-nitrophenyl, 4-chloro-2-nitrophenyl, 4-chloro-3-nitrophenyl, 5-chloro-2-nitrophenyl, 3-methyl-4-nitro phenyl, 3-methoxy-4-nitrophenyl, 2-methylthio-4-nitrophenyl, 2,4-dinitrophenyl or 3,4-dinitrophenyl, and A is ethylene or trimethylene.

5. The compound claimed in claim 2, in which $R^1$ and $R^2$ are each methyl, $R^3$ is methyl or ethyl, the group of the formula:

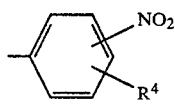

is 4-nitrophenyl, 2-chloro-4-nitrophenyl, 4-chloro-2-nitrophenyl or 3-methyl-4-nitrophenyl, and A is ethylene.

6. The compound claimed in claim 2, in which $R^1$, $R^2$ and $R^3$ are each methyl, the group of the formula:

is 4-nitrophenyl, 2-chloro-4-nitrophenyl, 4-chloro-2-nitrophenyl or 3-methyl-4-nitrophenyl, and A is ethylene.

7. A cis isomer of the compound claimed in claim 1, 3 or 6.

8. A (+)-cis isomer of the compound claimed in claim 1, 3 or 6.

9. The compound claimed in claim 6, which is (+)-cis-2-(4-methoxyphenyl)-3-(2-chloro-4-nitrobenzoyloxy)-5-[2-(dimethylamino)ethyl]-2,3-dihydro-1,5-benzothiazepin-4(5H)-one or a pharmaceutically acceptable acid addition salt thereof.

10. The compound claimed in claim 6, which is (+)-cis-2-(4-methoxyphenyl)-3-(4-nitrobenzoyloxy)-5-[2-(dimethylamino)ethyl]-2,3-dihydro-1,5-benzothiazepin-4(5H)-one or a pharmaceutically acceptable acid addition salt thereof.

11. The compound claimed in claim 6, which is (+)-cis-2-(4-methoxyphenyl)-3-(4-chloro-2-nitrobenzoyloxy)-5-[2-(dimethylamino ethyl]-2,3-dihydro-1,5-benzothiazepin-4(5H)-one or a pharmaceutically acceptable acid addition salt thereof.

12. The compound claimed in claim 6, which is (+)-cis-2-(4-methoxyphenyl)-3-(3-methyl-4-nitrobenzoyloxy)-5-[2-(dimethylamino)ethyl]-2,3-dihydro-1,5-benzothiazepin-4(5H)-one or a pharmaceutically acceptable acid addition salt thereof.

13. A pharmaceutical composition which comprises a therapeutically effective amount of a compound of the formula:

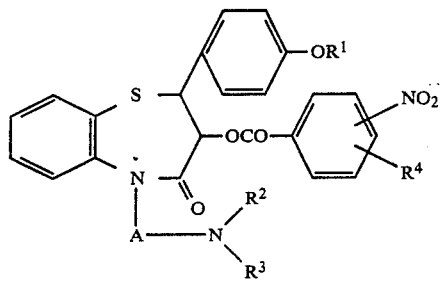

(I)

wherein $R^1$ and $R^2$ are each lower alkyl, $R^3$ is hydrogen, lower alkyl or hydroxy-lower alkyl, $R^4$ is hydrogen, halogen, lower alkyl, lower alkoxy, lower alkylthio or nitro, and A is lower alkylene, or a pharmaceutically acceptable acid addition salt thereof and a pharmaceutically acceptable carrier therefor.

14. A method of producing a cerebral vasodilating effect on a warm-blooded animal comprising administering to said warm-blooded animal an effective amount of the compound claimed in claim 1.

15. A method of producing a coronary vasodilating effect on a warm-blooded animal comprising administering to said warm-blooded animal an effective amount of the compound claimed in claim 1.

* * * * *